United States Patent [19]

Hara et al.

[11] 4,241,154

[45] Dec. 23, 1980

[54] METHOD OF STABILIZING ORGANIC SUBSTRATES AGAINST THE ACTION OF LIGHT

[75] Inventors: Hiroshi Hara, Asaka; Yoshiaki Suzuki, Minami-ashigara, both of Japan

[73] Assignee: Fuji Photo Film Co., Ltd., Minami-ashigara, Japan

[21] Appl. No.: 956,303

[22] Filed: Oct. 30, 1978

[30] Foreign Application Priority Data

Oct. 28, 1977 [JP] Japan ................. 52-129349

[51] Int. Cl.³ ............................. G03C 7/00
[52] U.S. Cl. ..................... 430/17; 430/216; 430/372; 430/384; 430/386; 430/388; 430/551; 430/552; 430/554; 430/556; 430/558; 430/933; 430/955; 260/37 R; 260/429 R
[58] Field of Search ............. 96/56, 110, 84 R, 67, 96/66.4, 109, 119, 114.5, 100, 99; 252/300 R; 260/429 R, 429 C, 429 J, 438.1, 439 R, 37 R; 430/17, 216, 372, 551, 933

[56] References Cited

U.S. PATENT DOCUMENTS

| | | | |
|---|---|---|---|
| 3,494,945 | 2/1970 | Lewis et al. | 260/439 R |
| 3,499,887 | 3/1970 | Cooper et al. | 260/429 R |
| 3,536,492 | 10/1970 | Luchs | 96/110 |
| 3,885,966 | 5/1975 | Gracia et al. | 96/94 R |
| 4,050,938 | 9/1977 | Smith, Jr. et al. | 96/84 UV |
| 4,076,531 | 2/1978 | Crowell | 96/94 R |

OTHER PUBLICATIONS

Fackler et al., Journal of the American Chemical Society, vol. 88, pp. 3913-3920, (1966).
Photographic Gelatin, Croome et al., Focal Press, N.Y., © 1965, pp.76-83.
Stabilization of Photographic Silver Halide Emulsions-Birr Focal Press, © 1974, pp. 115-117.
Photographic Emulsions, James, NDC, Park Ridge, N.J. © 1973, pp. 24 to 27.
Mech. of Oxid. Photodegradation and of UV Stabilization of Polyolefins, Cicchetti, Adv. Polymer. Sci., vol. 7, pp. 70-112 (1970).

*Primary Examiner*—J. Travis Brown
*Attorney, Agent, or Firm*—Sughrue, Rothwell, Mion, Zinn and Macpeak

[57] ABSTRACT

The stability of organic substrate materials having an absorption peak between 300 and 800 nm in wavelength can be improved by the presence of a compound represented by the following general formula (I),

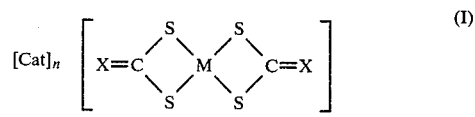

wherein M represents Cu, Co, Ni, Pd or Pt atom; Cat represents a divalent cation or two monovalent cations; X represents S or a

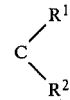

group where $R^1$ and $R^2$ each represents a CN, a $COR^3$, a $COOR^4$, a $CONR^5R^6$, or a $SO_2R^7$ group and $R^1$ may combine with $R^2$ to form a 5- or 6-membered ring; $R^3$, $R^4$ and $R^7$ each represents an alkyl or an aryl group, $R^5$ and $R^6$ each represents a hydrogen atom, an alkyl or an aryl group, and n represents an integer of 1 or 2.

12 Claims, No Drawings

METHOD OF STABILIZING ORGANIC SUBSTRATES AGAINST THE ACTION OF LIGHT

BACKGROUND OF THE INVENTION

1. Field of the Invention

The present invention relates to improving the light fastness of organic substrate materials and more particularly to improving the light fastness of organic compounds useful as dyestuffs. The present invention is particularly directed to improving the light fastness of organic substrate materials occurring in photographic materials, e.g., color films, prints, etc.; in colored polymers useful as agricultural vinyl cover sheets, umbrellas, tents, etc.; of fluorescent whitening agents; and dyed textiles, etc.

2. Description of the Prior Art

It is commonly accepted that organic substances such as, for example, organic dyes tend to fade upon exposure to light. Extensive studies are being carried out in various technical fields such as in printing inks, textile dyeing as well as in color photography, in an effort to improve the light fastness of the organic dyes.

The present invention is advantageously used to improve the light fastness of such organic substrates.

In the following description, the term "organic substrate material" or "organic substrate" means a material appearing colored to the human eye under the illumination of sunlight, including not only those compounds having absorption peaks in the visible region of spectrum, but those with absorption peaks which lie in the infrared region or in the ultraviolet region, such as optical whitening agent. In other words, the organic substrate materials of the present invention include those organic colorants having the absorption peaks at the wavelength of from 300 to 800 nm.

In the present specification, the term "dye" or "dyestuff" means an organic material which appears colored to the human eye under the illumination of sunlight.

In the present specification, the term "light" conceptually includes electromagnetic radiation with wavelengths up to about 800 nm, thus including ultraviolet rays below 400 nm, visible light of from about 400 nm to about 700 nm and infrared radiation of from about 700 to about 800 nm.

It is well known that organic substrate materials such as, for example, dyes or coloring agents tend to fade by the action of light; and a number of publications dealing with the methods of suppressing tendency or improving the light fastness of such materials are known. For example, U.S. Pat. No. 3,432,300 discloses that the light fastness of organic compounds such as indophenol, indoaniline, azo and azomethine dyes against visible and UV light can be improved using phenol derivatives containing a condensed heterocyclic structure. "The Theory of the Photographic Process" authored by Mees et al (3rd edition-1967) teaches in Chapter 17, that silver halide color photographic materials generally give rise to axomethine or indoaniline dyes resulting upon the reaction of the oxidation product from an aromatic primary amine developing agent with a color coupler. Various patents also describe how to improve the stability to light of color photographic images thus obtained. Compounds which are effective for the improvement of the light fastness of the co-existing dye include, for example, the hydroquinone derivatives set forth in U.S. Pat. Nos. 2,360,290, 2,418,613, 2,675,314, 2,701,197, 2,704,713, 2,728,659, 2,732,300, 2,735,765, 2,710,801 and 2,816,028 and Brit. Pat. No. 1,363,921, etc., gallic acid derivatives set forth in U.S. Pat. Nos. 3,457,079 and 3,069,262, Japan. Pat. Appl. (OPI) No. 13,496/1968, etc., p-alkoxyphenols set forth in U.S. Pat. Nos. 2,735,765 and 3,698,909, chroman and coumarane derivatives set forth in U.S. Pat. Nos. 3,432,300, 3,574,626, 3,698,909, 3,573,050 and 4,015,990, etc. These compounds are effective in preventing fading or discoloration of dye images to a certain extent, but are not as satisfactory as would be desired.

Brit. Pat. No. 1,451,000 discloses that the stability to light of organic substrate materials is enhanced by the use of azomethine quenching compounds which have their absorption peaks at a longer wavelength than the substrate material. Unfortunately, the azomethine quenching compound is colored itself and adversely affects the color hue of the substrate material. Metal chelates can be used to prevent the degradation of polymeric materials caused by the action of light as is described in the following literature; J. P. Guillory & R. S. Becker, *J. Polym. Sci.*, Polym. Chem. Ed., 12, 993 (1974), and R. P. R. Ranaweera & G. Scott, *J. Polym. Sci.*, Polym. Let. Ed., 13, 71 (1975), etc. Stabilization of dyes against light by the use of metal chelates is also set forth in U.S. Pat. No. 4,050,938, Published Japanese Patent Application (OPI) No. 87,649/1975 and Research Disclosure 15162 (1976). However, the disclosed metal chelates do not exhibit a satisfactory fade preventing effect and when the metal chelates are employed in a photographic emulsion for practical use the disclosed metal chelates desensitize the silver halide probably due to an undesirable interaction with silver. Also the metal chelates exhibit an undesirably poor solubility in organic solvents. The latter property limits the working concentration of such a chelate to amounts which are too low to provide sufficient fade prevention. Moreover, these chelates cannot be present in a high concentration since they themselves are colored and they adversely affect the color hue and the color purity of the dyes.

Furthermore, heretofore agents suitable for preventing the fading of cyan dyes have not been known.

SUMMARY OF THE INVENTION

Accordingly, one object of the present invention is to provide a method of stabilizing organic substrate materials against the action of light.

Another object of the instant invention is to provide a method of improving the stability of these materials against light without deteriorating the color hue as well as the color purity of organic substrate materials such as, in particular, dyes or coloring agents.

Still another object of the instant invention is to provide a method of enhancing the stability of organic substrate materials against light by using stabilizing agents which are readily soluble in organic solvents and which are highly compatible with organic substrate materials.

Another object of the present invention is to provide a method of improving the stability against light of dye images composing color photographs.

Another object of the instant invention is to provide a method of improving the stability against the action of light of dyestuffs resulting from the reaction of an aromatic primary amine developing agent with a color coupler.

Still another object of the present invention is to improve the light fastness of colored polymers useful as agricultural vinyl cover sheets, umbrellas, tents, etc.

Another object of this invention is to improve the light fastness of cyan dyes and especially cyan color photographic images.

Still other objects of the present invention will become clear from the following descriptions of the specification.

DETAILED DESCRIPTION OF PREFERRED EMBODIMENTS

The above mentioned and other objects of the present invention have been achieved by making co-existant with the organic substrate material one compound represented by the following general formula (I)

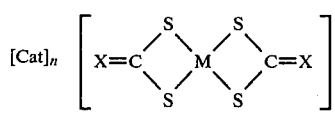
(I)

In the formula, M represents a metal atom selected from the group consisting of Cu, Co, Ni, Pd and Pt. Cat represents a divalent organic or inorganic cation or two monovalent organic or inorganic cations, and X represents a

group or a sulfur atom.

Each of $R^1$ and $R^2$ represents CN or a group represented by $COR^3$, $COOR^4$, $CONR^5R^6$, or $SO_2R^7$. $R^1$ and $R^2$ may combine to form the non-metallic atoms necessary to complete a 5- or 6-membered ring structure. $R^3$, $R^4$ and $R^7$ represent an alkyl group, substituted or unsubstituted straight or branched chain, with from 1 to 20 carbon atoms, or an aryl group, substituted or unsubstituted, with from 6 to 10 carbon atoms.

$R^5$ and $R^6$ represent a hydrogen atom, a substituted or unsubstituted alkyl group, with from 1 to 20 carbon atoms, or a substituted or unsubstituted aryl group, with from 6 to 10 carbon atoms, and n represents an integer of 1 or 2.

The terms "in the presence or" or "coexistant with" as used in the specification refer not only to co-existence of the substrate material and the compound of the formula (I) in the same solution, dispersion, emulsion or layer but also to the existence of the organic substrate and the complex in adjacent layers of a multi-layered photographic material. As long as the complex compound is associated with the organic substrate material such that it improves the light fastness of the organic substrate it is used "in the presence of" or "coexists" with the substrate for purposes of the present invention.

Suitable inorganic, divalent cations represented by Cat in formula (I) include alkaline earth metals such as Mg, Ca, Sr, Ba, etc. Suitable organic, divalent cations represented by Cat in formula (I) include bis-onium ions such as, for example, bis-ammonium ion, bis-phosphonium ion, etc.

Suitable inorganic, monovalent cations represented by Cat in formula (I) include alkali metal ions (e.g., Li$^+$, Na$^+$, K$^+$, etc.), or NH$_4$$^+$. Corresponding organic ions include onium ions (e.g., quarternary ammonium ion, quarternary phosphonium ion, tertiary sulfonium ion, etc.).

Among the onium ions cited above, those particularly suited for the instant invention include those represented by the following general formulae (Ia), (Ib), (Ic), (Id) and (Ie).

(Ia)

(Ib)

(Ic)

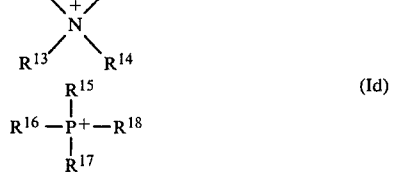
(Id)

(Ie)

In these formulae, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$ and $R^{21}$ each represents a straight chain or branched chain alkyl group, substituted or unsubstituted, having from 1 to 20 carbon atoms, or an aryl group, substituted or unsubstituted, having from 6 to 14 carbon atoms. Substituted or unsubstituted alkyl groups, having 1 to 20 carbon atoms include, for example, methyl, ethyl, n-butyl, iso-amyl, n-dodecyl, n-octadecyl, etc., while the aryl groups are monocyclic or bicyclic with from 6 to 14 carbon atoms include phenyl, tolyl, α-naphthyl, anisil, etc.

Such an alkyl or an aryl group may be substituted with any of the following groups; cyano, an alkyl group with from 1 to 20 carbon atoms (e.g., methyl, ethyl, n-butyl, n-octyl, etc.), an aryl group with from 6 to 14 carbon atoms (e.g., phenyl, tolyl, α-naphthyl, etc.), an alkoxy group (e.g., methoxy, ethoxy, propoxy, butoxy, etc.), an aryloxy group (e.g., phenoxy, tolyloxy, etc.), an alkoxycarbonyl group (e.g., methoxycarbonyl, ethoxycarbonyl, n-butoxycarbonyl, etc.), an aryloxycarbonyl group (e.g., phenoxycarbonyl, tolyloxycarbonyl, etc.), an acyl group (e.g., acetyl, benzoyl, lauroyl, etc.), an acylamino group (e.g., acetylamino, benzoylamino, etc.), a carbamoyl group (e.g., N-ethylcarbamoyl, N-phenylcarbamoyl, N-hexylcarbamoyl, etc.), an alkylsulfonylamino group (e.g., methylsulfonylamino, phenylsulfonylamino, butylsulfonylamino, etc.), a sulfonyl group (e.g., mesyl, tosyl, etc.), etc. wherein the alkyl portion of said alkoxy group, acyl group, carbamoyl group, etc. contains 1 to 20 carbon atoms and the aryl moiety of said aryloxy group, acyl group, etc. contains 6 to 10 carbon atoms.

$Z^1$ and $Z^2$ each represents non-metallic atoms necessary to complete a 5- or 6-membered ring. Suitable 5- or 6-membered rings include pyridine, imidazole, pyrrole, 2-pyrroline, pyrrolidine, piperidine, pyrazole, pyrazoline, imidazoline, etc.

Examples of cations represented by general formula (Ib) are dodecylpyridinium, hexadecylpyridinium, dodecylimidazolium, etc. Examples of cations represented by general formula (Ic) are N-ethyl-N-hexadecylpiperidinium, N-ethyl-N-dodecylpyrazolidinium, etc.

Particularly suited positive ions for the present invention represented by Cat in general formula (I) are $Na^+$, $NH_4^+$ and those represented by general formulae (Ia), (Ib) and (Id).

Alkyl groups represented by $R^3$, $R^4$, $R^5$, $R^6$ and $R^7$ are branched or straight-chained including from 1 to 20 carbon atoms include, for example, methyl, ethyl, propyl, butyl, amyl, hexyl, octyl, decyl, dodecyl, tetradecyl, hexadecyl, heptadecyl, octadecyl, etc. Aryl groups represented by $R^3$, $R^4$, $R^5$, $R^6$ and $R^7$ are monocyclic or bicyclic aryl groups having from 6 to 10 carbon atoms include, for example, phenyl, naphthyl, etc. Note that when the aryl group is substituted with an alkyl group or the like the alkyl group may contain 1 to 20 carbon atoms.

Suitable groups which may be substituted on the alkyl group with from 1 to 20 carbon atoms and on the aryl group with from 6 to 10 carbon atoms designated as $R^3$, $R^4$, $R^5$, $R^6$ or $R^7$ include, for example, halogen atoms (Cl, Br, or F), CN, a straight-chained or branched $C_1$–$C_{20}$ alkyl group (methyl, ethyl, propyl, butyl, hexyl, octyl, decyl, dodecyl, tetradecyl, hexadecyl, heptadecyl, octadecyl, etc.), a monocyclic or bicyclic aryl group (phenyl, naphthyl, etc.), an alkoxy group (methoxy, ethoxy, butoxy, propoxy, etc.), an aryloxy group (phenoxy, tolyloxy, naphthoxy, etc.), an alkoxycarbonyl group (methoxycarbonyl, butoxycarbonyl, etc.), an aryloxycarbonyl group (phenoxycarbonyl, tolyloxycarbonyl, etc.), an acyl group (formyl, acetyl, valeryl, stearoyl, benzoyl, toluoyl, naphthoyl, etc.), an acylamino group (acetamide, benzoylamide, etc.), an alkylamino group (n-butylamino, N,N-diethylamino, etc.), an anilino group (phenylamino, N-methylanilino, N-phenylanilino, N-acetylanilino, etc.), a carbamoyl group (butylcarbamoyl, diethylcarbamoyl, etc.), a sulfamoyl group (N-butylsulfamoyl, N,N-diethylsulfamoyl, N-dodecylsulfamoyl, etc.), an alkyl or aryl sulfonylamino group (methylsulfonylamino, phenylsulfonylamino, etc.), an alkyl or aryl sulfonyl group (mesyl, tosyl, etc.), etc., wherein the alkyl and aryl moieties of these substituents have the number of carbon atoms defined above for the primary substituents.

5- and 6-membered ring structures completed by the coupling of $R^1$ and $R^2$ contained in the compound represented by general formula (I) include, for example, 1,3-indanedione, barbituric acid, 1,2-diaza-3,5-dioxocyclopentane, 2-thiobarbituric acid, 1,3-cyclohexanedione, 2,4-diaza-1-alkoxy-3,5-dioxocyclohexene, 2,4-thiazolidinedione, 2-iminothiazolidine-4-one, hydantoin, 2,4-oxazolidinedione, 2-iminoxazolidine-4-one, 2-iminoimidazolidine-4-one and the like.

Among the compounds represented by general formula (I), those represented by the following general formulae (If), (Ig), (Ih) and (Ii) are especially well adapted for use in the present invention.

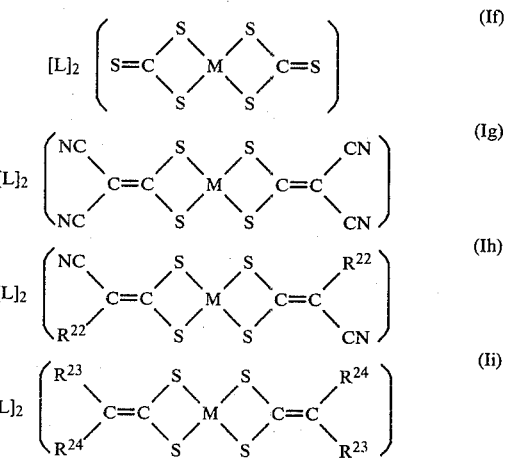

where M represents a metal atom selected from Cu, Co, Ni, Pd and Pt. L represents Li, Na, K, a tetra-alkylammonium ion with $C_1$–$C_{18}$ alkyl groups, or a tetra-alkylphosphonium ion with $C_1$–$C_{18}$ alkyl groups.

$R^{22}$, $R^{23}$ and $R^{24}$ each represents an acyl group (e.g., n-capryloyl, n-stearoyl, n-dodecylbenzoyl, etc.), an alkoxycarbonyl group (e.g., methoxycarbonyl, ethoxycarbonyl, butoxycarbonyl, etc.), an alkylsulfonyl group (e.g., mesyl, ethansulfonyl, butanesulfonyl, dodecanesulfonyl, benzenesulfonyl, etc.), or a carbamoyl group (e.g, carbamoyl, N-ethylcarbamoyl, N-phenylcarbamoyl, etc.). $R^{23}$ and $R^{24}$ may combine to form a 5- or 6-membered ring including, for example, thiazoline-5-ylidene, indane-1,3-dione-2-ylidene, 2,4,6-trioxypyrimidine-5-ylidene, etc. preferably thiazoline and pyrimidine).

The following compounds which all belong to the category defined by general formula (I) are shown for the purpose of illustrating typical metal chelate compounds particularly effective to embody the instant invention, but not for the purpose of limiting the scope of the invention.

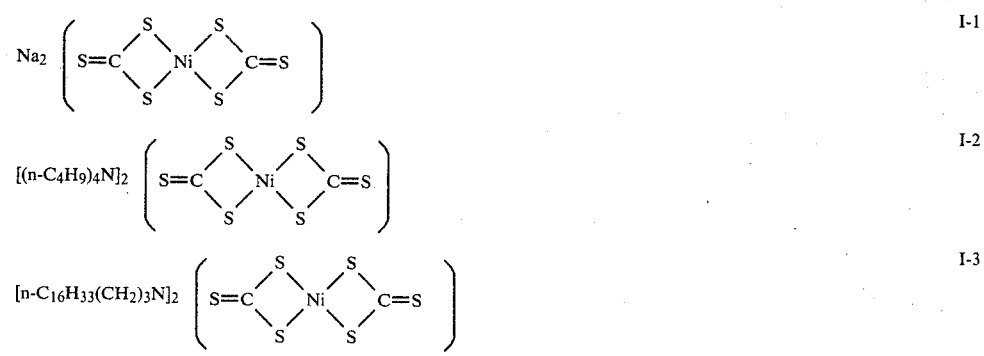

-continued

| | | |
|---|---|---|
| $[n\text{-}C_{16}H_{33}(nC_4H_9)_3P]_2$ | [Ni(S=C-S)_2 complex] | I-4 |
| $[n\text{-}C_{16}H_{33}(CH_3)_3N]_2$ | [Cu(S=C-S)_2 complex] | I-5 |
| $[n\text{-}C_{16}H_{33}(CH_3)_3N]_2$ | [Co(S=C-S)_2 complex] | I-6 |
| $[n\text{-}C_{16}H_{33}(CH_3)_3N]_2$ | [Pd(S=C-S)_2 complex] | I-7 |
| $[n\text{-}C_{16}H_{33}(CH_3)_3N]_2$ | [Pt(S=C-S)_2 complex] | I-8 |
| $Na_2$ | [Ni(S_2C_2(CN)_2)_2] | I-9 |
| $[(n\text{-}C_4H_9)_4N]_2$ | [Ni(S_2C_2(CN)_2)_2] | I-10 |
| $[n\text{-}C_{16}H_{33}(CH_3)_3N]_2$ | [Ni(S_2C_2(CN)_2)_2] | I-11 |
| $\{n\text{-}C_{16}H_{33}(CH_3)_2(CH_2C_6H_5)N\}_2$ | [Ni(S_2C_2(CN)_2)_2] | I-12 |
| $[\{n\text{-}C_{15}H_{31}CONH(CH_2)_3\}(CH_3)_3N]_2$ | [Ni(S_2C_2(CN)_2)_2] | I-13 |
| $[\{nC_{10}H_{21}O(CH_2)_3\}(CH_3)_3N]_2$ | [Ni(S_2C_2(CN)_2)_2] | I-14 |
| $[\{n\text{-}C_{10}H_{21}O_2C(CH_2)_2\}(CH_3)_3N]_2$ | [Ni(S_2C_2(CN)_2)_2] | I-15 |
| $[(n\text{-}C_{12}H_{25}\text{-}C_6H_4\text{-}CH_2(CH_3)_3N]_2$ | [Ni(S_2C_2(CN)_2)_2] | I-16 |
| $[n\text{-}C_{16}H_{33}(n\text{-}C_4H_9)_3P]_2$ | [Ni(S_2C_2(CN)_2)_2] | I-17 |
| $[n\text{-}C_{16}H_{33}(CH_3)_3N]_2$ | [Ni complex with CN and CONH_2 groups] | I-18 |

-continued

| | | |
|---|---|---|
| I-19 | $Na_2\left\{\begin{array}{c}NC\\H_5C_2O_2C\end{array}C=C\begin{array}{c}S\\S\end{array}Ni\begin{array}{c}S\\S\end{array}C=C\begin{array}{c}CO_2C_2H_5\\CN\end{array}\right\}$ | |
| I-20 | $[(n\text{-}C_4H_9)_4N]_2\left\{\begin{array}{c}NC\\n\text{-}C_{16}H_{33}O_2C\end{array}C=C\begin{array}{c}S\\S\end{array}Ni\begin{array}{c}S\\S\end{array}C=C\begin{array}{c}CO_2n\text{-}C_{16}H_{33}\\CN\end{array}\right\}$ | |
| I-21 | $[n\text{-}C_{16}H_{33}(CH_3)_3N]_2\left\{\begin{array}{c}n\text{-}C_{18}H_{37}O_2C\\CH_3OC\end{array}C=C\begin{array}{c}S\\S\end{array}Ni\begin{array}{c}S\\S\end{array}C=C\begin{array}{c}COCH_3\\CO_2n\text{-}C_{18}H_{37}\end{array}\right\}$ | |
| I-22 | $[n\text{-}C_{16}H_{33}(CH_3)_3N]_2\left\{\begin{array}{c}NC\\C_2H_5O_2C\end{array}C=C\begin{array}{c}S\\S\end{array}Ni\begin{array}{c}S\\S\end{array}C=C\begin{array}{c}CO_2C_2H_5\\CN\end{array}\right\}$ | |
| I-23 | $[n\text{-}C_{16}H_{33}\text{-}N\bigcirc]_2\left\{\begin{array}{c}NC\\C_2H_5O_2C\end{array}C=C\begin{array}{c}S\\S\end{array}Ni\begin{array}{c}S\\S\end{array}C=C\begin{array}{c}CO_2C_2H_5\\CN\end{array}\right\}$ | |
| I-24 | $[n\text{-}C_{16}H_{33}(N\text{-}C_4H_9)_3P]_2\left\{\begin{array}{c}NC\\C_2H_5O_2C\end{array}C=C\begin{array}{c}S\\S\end{array}Ni\begin{array}{c}S\\S\end{array}C=C\begin{array}{c}CO_2C_2H_5\\CN\end{array}\right\}$ | |
| I-25 | $Na_2\left\{\begin{array}{c}C_2H_5O_2C\\C_2H_5O_2C\end{array}C=C\begin{array}{c}S\\S\end{array}Ni\begin{array}{c}S\\S\end{array}C=C\begin{array}{c}CO_2C_2H_5\\CO_2C_2H_5\end{array}\right\}$ | |
| I-26 | $[(n\text{-}C_4H_9)_4N]_2\left\{\begin{array}{c}n\text{-}C_8H_{17}O_2C\\n\text{-}C_8H_{17}O_2C\end{array}C=C\begin{array}{c}S\\S\end{array}Ni\begin{array}{c}S\\S\end{array}C=C\begin{array}{c}CO_2n\text{-}C_8H_{17}\\CO_2n\text{-}C_8H_{17}\end{array}\right\}$ | |
| I-27 | $[n\text{-}C_{16}H_{33}(CH_3)_3N]_2\left\{\begin{array}{c}C_2H_5O_2C\\C_2H_5O_2C\end{array}C=C\begin{array}{c}S\\S\end{array}Ni\begin{array}{c}S\\S\end{array}C=C\begin{array}{c}CO_2C_2H_5\\CO_2C_2H_5\end{array}\right\}$ | |
| I-28 | $[n\text{-}C_{16}H_{33}(n\text{-}C_4H_9)_3P]_2\left\{\begin{array}{c}C_2H_5O_2C\\C_2H_5O_2C\end{array}C=C\begin{array}{c}S\\S\end{array}Ni\begin{array}{c}S\\S\end{array}C=C\begin{array}{c}CO_2C_2H_5\\CO_2C_2H_5\end{array}\right\}$ | |
| I-29 | $Na_2\left\{\begin{array}{c}C_2H_5O_2S\\C_2H_5O_2C\end{array}C=C\begin{array}{c}S\\S\end{array}Ni\begin{array}{c}S\\S\end{array}C=C\begin{array}{c}CO_2C_2H_5\\SO_2C_2H_5\end{array}\right\}$ | |
| I-30 | $[(n\text{-}C_{12}H_{25}C_6H_4CH_2)(CH_3)_3N]_2\left\{\begin{array}{c}C_2H_5O_2S\\C_2H_5O_2C\end{array}C=C\begin{array}{c}S\\S\end{array}Ni\begin{array}{c}S\\S\end{array}C=C\begin{array}{c}CO_2C_2H_5\\SO_2C_2H_5\end{array}\right\}$ | |
| I-31 | $[(n\text{-}C_4H_9)_4N]_2\left\{\begin{array}{c}n\text{-}C_{18}H_{37}O_2C\\n\text{-}C_{18}H_{37}O_2C\end{array}C=C\begin{array}{c}S\\S\end{array}Ni\begin{array}{c}S\\S\end{array}C=C\begin{array}{c}CO_2n\text{-}C_{18}H_{37}\\CO_2n\text{-}C_{18}H_{37}\end{array}\right\}$ | |
| I-32 | $[n\text{-}C_{16}H_{33}(CH_3)_3N]_2\left\{\begin{array}{c}n\text{-}C_3F_7O_2C\\n\text{-}C_3F_7O_2C\end{array}C=C\begin{array}{c}S\\S\end{array}Ni\begin{array}{c}S\\S\end{array}C=C\begin{array}{c}CO_2n\text{-}C_3F_7\\CO_2nC_3F_7\end{array}\right\}$ | |
| I-33 | $[n\text{-}C_{16}H_{33}(CH_3)_3N]_2\left\{\begin{array}{c}CH_3OC\\CH_3OC\end{array}C=C\begin{array}{c}S\\S\end{array}Ni\begin{array}{c}S\\S\end{array}C=C\begin{array}{c}COCH_3\\COCH_3\end{array}\right\}$ | |

-continued

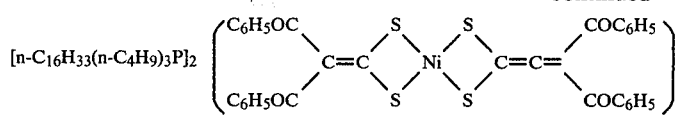
I-34

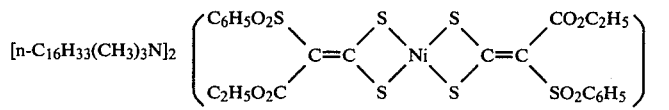
I-35

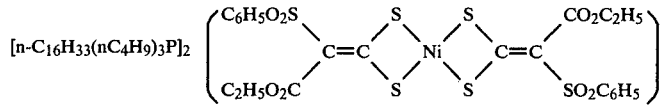
I-36

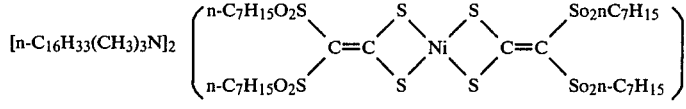
I-37

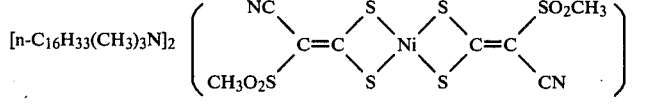
I-38

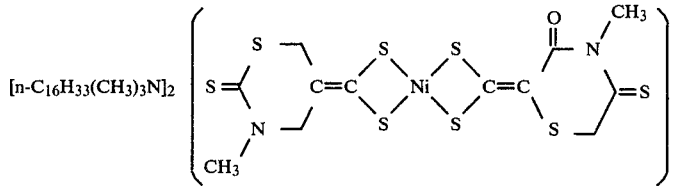
I-39

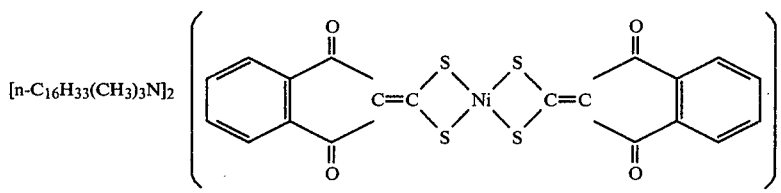
I-40

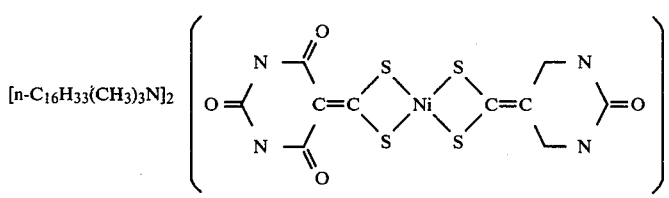
I-41

The synthetic procedures for these chelate complexes are set forth in, for example, the following reports; J. P. Fackler, Jr., D. Coucouvanis, J. A. C. S., 88, 3913 (1966) and D. Coucouvanis, J. P. Fackler, J. A. C. S. 89 1346 (1967). Na$_2$(S$_2$C=X), synthesized in accordance with the methods of R. Compper and W. Tophl infra, and a metal chloride are reacted in an alcohol. Then, an alcohol solution of a quarternary salt is added to the resulting solution at room temperature with stirring to precipitate crystals, followed by filtering the crystals. If desired, recrystalization may be carried out.

SYNTHESIS EXAMPLE 1

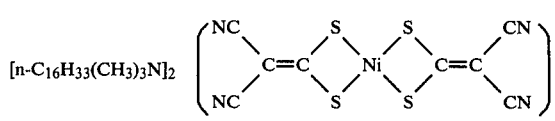

Into 60 ml methanol was dissolved 9.3 g Na$_2$[S$_2$C=C(CN)$_2$] prepared in advance according to the method described in Chem, Ber., 75, 2861 (1962) by R. Compper and W. Tophl; to the resulting solution was added dropwise with agitation a solution obtained by dissolving 5.94 g nickel chloride hexahydrate in 40 ml methanol. After completion of the addition, another one hour agitation was continued at room temperature. The mixture was filtered. A solution obtained by dissolving 18.2 g [n—C$_{16}$H$_{33}$(CH$_3$)$_3$N]Br into 30 ml methanol was added dropwise to the filtrate with stirring. Gold-colored crystals precipitated.

After another half hour of agitation, the precipitate was collected by filtration, and recrystallized from methanol to produce a 15 g yield.

SYNTHESIS EXAMPLE 2

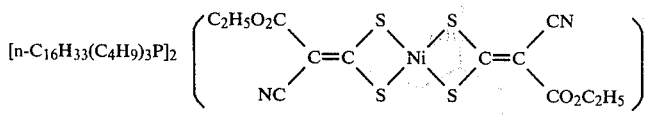

Into 100 ml water was dissolved 20.1 g

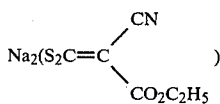

prepared in advance according to the method described in the literature cited in the Synthesis Example 1. To the resulting solution was added dropwise at room temperature a solution comprising 11.9 g nickel chloride hexahydrate dissolved in 80 ml methanol. After further agitation for one hour, the solution was filtered. 63 g[n—$C_{16}H_{33}$(n—$C_4H_9$)$_4$P]Br dissolved in 80 ml methanol was added to the filtrate. Agitation was continued for 30 min. after the completion of addition, and the crystalline product formed was collected by filtration. The yield after recrystallization from methanol was 35 g.

The organic substrate material of the present invention includes all dyestuffs belonging to various categories encountered in textile dyeing; i.e., water-soluble dyes such as basic, acid, direct, water-soluble vat, and mordant dyes, etc.; water-insoluble dyes such as sulfur, vat, oil-soluble, dispersion, azoic, oxidative dyes,; and reactive dyes. Not only compounds which appear colored under the illumination of sunlight, but also colorless or pale yellow compounds such as fluorescent whitening agents are included within the organic substrate material defined in the present invention.

Dyestuffs which are particularly suited for the application of the present invention include quinoneimine dyes (e.g., azine, oxazine, or thiazine dyes, etc.), methine or polymethine dyes (e.g. cyanine, azomethine, and other dyes), azo dyes, azomethine dyes, anthraquinone dyes, indo-amine dyes, indophenol dyes, indigoid dyes, carbonium dyes, formazane dyes, etc., classified according to chemical structure.

The organic substrate material associated with the instant invention includes particularly the dyes composing photographic images. Including, for example, those resulting from a color coupler, a DRR (dye releasing redox) compound, a DDR (diffusible dye releasing) coupler, an amidolazone derivative dye developer, etc., those used for silver dye bleach process, etc. More specifically, anthraquinone, quinoneimine, azo, methine, polymethine, indoamine, indophenol and formazane types of dyes frequently formed in the photographic material are particularly suited for the application of the instant invention. Further, most favorable photographic dyestuffs are methine and polymethine type ones, and indo-amine and indophenol dyes, all of which have in their chemical structure the following group.

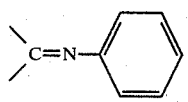

The phenyl group in the above expression may be substituted with and alkyl, and alkoxy, a halogen, or an amino group, etc.

Dye forming couplers used in the instant invention include those capable of providing yellow, cyan and magenta dye images. Such couplers may be so-called 4-equivalent or 2-equivalent couplers disclosed in, for example, U.S. Pat. Nos. 3,277,155 and 3,458,315.

In general, yellow dye forming couplers have at least one methylene group activated by a carbonyl group (e.g., an openchain ketomethylene group), including β-diketone, β-ketoacylamide such as benzoylacetanilide and α-pivalylacetanilide. These types of coupler are set forth in, for example, U.S. Pat. Nos. 2,428,054, 4,026,706, 2,499,966, 2,453,661, 2,775,658, 2,908,573, 3,227,550, 3,253,924, 3,277,155 and 3,384,657 and Brit. Pat. 503,752.

Magenta dye image forming couplers exemplified by 5-pyrazolone derivatives can be used in conjunction with the instant invention. This type of coupler is described in, for example, U.S. Pat. Nos. 2,600,788, 2,725,292, 2,908,573, 3,006,759, 3,062,653, 3,152,896, 3,227,550, 3,252,924, 4,026,706 and 3,311,476. Other types of magenta dye forming couplers are indazolone derivatives as described in Vittum & Weissberger "Journal of Photographic Science"6. (1958), pp 158 U.S. Pat. No. 3,061,432 discloses pyrazolinobenzimidazole compounds. Also included are pyrazolo-s-triazoles set forth in Belgium Pat. No. 724,427, and 2-cyanoacetylcoumarone set forth in U.S. Pat. No. 2,115,394.

Cyan dye forming couplers within the perview of the present invention include phenol and α-naphthol derivatives which can form dyestuffs of the indaniline type upon reaction with the oxidized color developer. Such derivatives are disclosed in U.S. Pat. Nos. 2,275,292, 2,423,730, 2,474,293, 2,895,826, 2,908,573, 3,043,892, 4,026,706, 3,227,550 and 3,253,294.

General descriptions of these coupler compounds are also found in, "Encyclopedia of Chemical Technology" authored by Kirk and Othmer, Vol. 5, pp 822–825, and "Photographic Chemistry" authored by Glafkides, Vol. 2, pp 596–614.

As should be clear from the foregoing, the compounds of formula (I) are capable of improving light fastness for a wide variety of organic colorants or dyestuffs encountered both within and outside of the photographic art.

As is mentioned earlier, the method of the present invention is particularly suited for application in the photographic art and the dyes obtained upon the reaction of color couplers with the oxidation product from a primary aromatic amine developer for silver halide. Such developing agents include aminophenol as well as phenylenediamine, each of which can be used individually or in mixed forms. Typical developing agents which can react with various couplers to give organic substrate materials of the present invention include the following.

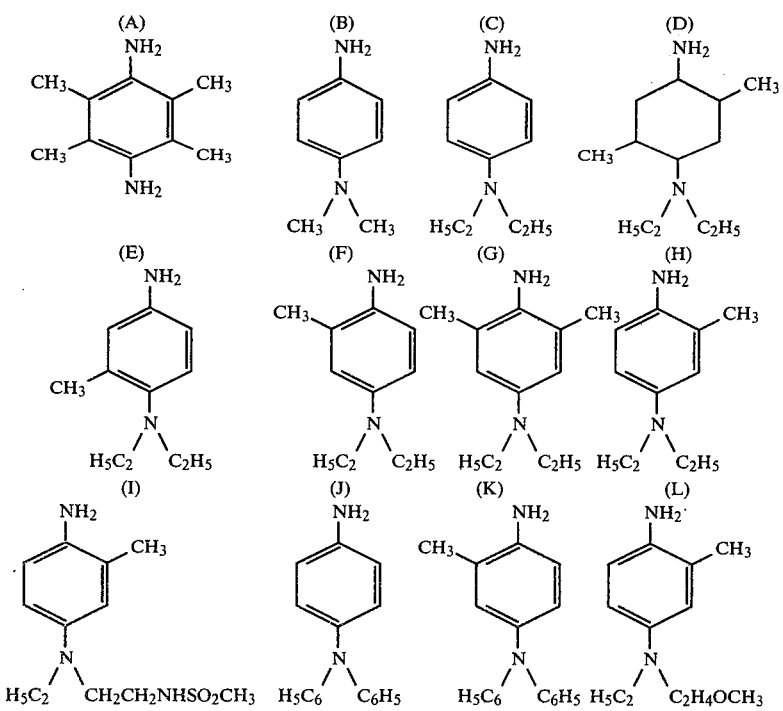

The developing agents illustrated above and others which can provide organic substrate material upon the reaction with color couplers. Cyan, magenta and yellow color couplers which are preferably employed are represented by the formula (IIA), (IIB) or (IIC) respectively:

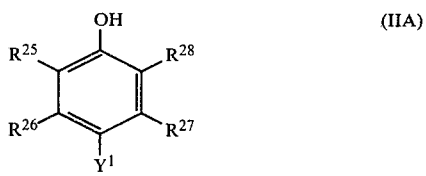

wherein $R^{25}$, $R^{26}$, $R^{27}$ and $R^{28}$ each represents a hydrogen atom, a halogen atom (e.g., fluorine, chlorine, bromine or iodine), an alkyl group having 1 to 20 carbon atoms (hereafter, all of the alkyl groups referred to with respect to formulae IIA, IIB, and IIC may possess 1 to 20 carbon atoms) (e.g., methyl, ethyl, octyl, dodecyl, tetradecyl, octadecyl, etc.); a carbamoyl wherein the aryl moiety has 6 to 10 carbon atoms, (hereafter all of the aryl groups referred to with respect to formulae IIA, IIB and IIC may possess 6 to 10 carbon atoms) (e.g., methylcarbamoyl, ethylcarbamoyl, dodecylcarbamoyl, tetradecylcarbamoyl, octadecylcarbamoyl, N-phenylcarbamoyl, N-tolylcarbamoyl, etc.); a sulfamoyl group (e.g., methylsulfamoyl, ethylsulfamoyl, dodecylsulfamoyl, tetradecylsulfamoyl, octadecylsulfamoyl, N-phenylsulfamoyl, N-tolylsulfamoyl, etc.); an amido group (e.g., acetamido, butylamido, benzamido, phenacetamido, etc.); a sulfonamido group (e.g., benzenesulfonylamido), a phosphoric acid amido group, a ureido group, etc.

$R^{25}$ and $R^{26}$ may combine with each other to form a six-membered carbocyclic ring (e.g., a benzene ring which may further be substituted with an alkyl or aryl group).

$Y^1$ represents a hydrogen atom, a halogen atom (e.g., fluorine, chlorine, bromine or iodine); or a group which is releasable upon the reaction with the oxidation product of a developing agent (e.g., an alkoxy group wherein the alkyl moiety has 1 to 20 carbon atoms, an aryloxy group wherein the aryl moiety has 6 to 10 carbon atoms, a sulfonamido group, a sulfonyl group, a carbamoyl group, an imido group, an aminosulfonyloxy group, an alkylcarbonyloxy group, an arylcarbonyloxy group, an alkylthio group, an arylthio group, a hereto ring thio group, etc.; the details of which are well known in the art.

The alkyl, carbamoyl, sulfamoyl and amido groups expressed by $R^{25}$, $R^{26}$, $R^{27}$ and $R^{28}$, or the 6-membered ring formed by combining $R^{25}$ and $R^{26}$ with each other can also be substituted with other substituents, for example, an alkyl group (e.g., methyl, ethyl, propyl, octyl, dodecyl, tetradecyl, octadecyl, etc.); an aryl group (e.g., phenyl, tolyl, naphthyl, etc.); an aryloxy group (e.g., phenoxy, 2,5-di-(t)-amylphenoxy, etc.); a halogen atom (e.g., chlorine, bromine, fluorine, etc.); and the like.

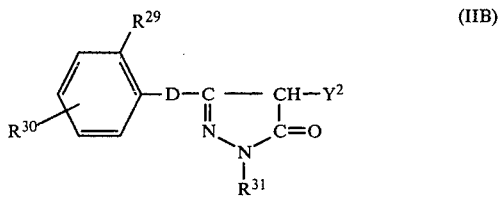

wherein $R^{29}$ represents a hydrogen atom, a halogen atom (e.g., chlorine, bromine, fluorine, etc.); an alkyl group (e.g., methyl, ethyl, n-propyl, etc.); or an alkoxy group (e.g., methoxy, ethoxy, etc.); $R^{30}$ represents an alkyl group (e.g., methyl, ethyl, octyl, dodecyl, tetradecyl, octadecyl, etc.); an amido group (e.g., butanamido decanamido, tetradecanamido, nonadecanamido, etc.); an imido group (e.g., tetradecylsuccinimido, octadecenylsuccinimido, etc.); an N-alkylcarbamoyl group (e.g., decylcarbamoyl, tetradecylcarbamoyl, octadecylcarbamoyl, etc.); an N-alkylsulfamoyl group (e.g., decylsulfamoyl, tetradecylsulfamoyl, octadecylsulfamoyl, etc.); an alkoxycarbonyl group (e.g., decyloxycarbonyl, tetradecyloxycarbonyl, octadecyloxycarbonyl, etc.); an acyloxy group (e.g., valeryloxy, palmitoyloxy, stearoyloxy, oleyloxy, benzoyloxy, toluoyloxy, etc.); a sulfonamido group, a urethane group, etc.; and $R^{31}$ represents an aryl group (e.g., phenyl, naphthyl, etc.. said alkyl and aryl groups having the number of carbon atoms discussed above with respect to formula IIA).

D represents an amino group, a carbonylamino group, or a ureido group. $Y^2$ represents a hydrogen atom, a halogen atom (e.g., chlorine, bromine, etc.); or a group which is releasable upon reaction with the oxidation product with a developing agent (e.g., an arylazo group, an aryloxy group, and acyloxy group, an alkylthio group, an arylthio group, etc.). Such groups are well known.

The alkyl or alkoxy group represented by $R^{29}$, the alkyl, amido, N-alkylcarbamoyl, N-alkylsulfamoyl, alkoxycarbonyl or acyloxy group represented by $R^{30}$, or the aryl group represented by $R^{31}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a halogen atom (e.g., chlorine, bromine, fluorine etc.), or the like.

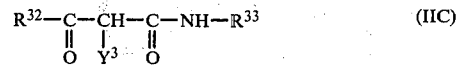

wherein $R^{32}$ represents an alkyl group (e.g., methyl, ethyl, (t)-butyl, (t)-octyl, etc.) or an aryl group (e.g., phenyl); and $R^{33}$ represents an aryl group (e.g., phenyl).

$Y^3$ represents a hydrogen atom, a halogen atom (e.g., chlorine, bromine, etc.), or a group which is releasable upon the reaction with the oxidation product of a developing agent, for example, a heterocyclic nuclei (e.g., naphthoimido, succinimido, 5,5-dimethylhydantoinyl, 2,4-oxazolidinedione residue, imido, pyridone residue, pyridazone residue, etc.), an acyloxy group, a sulfonyloxy group, an aryloxy group, a ureido group; which are well known in the art.

The alkyl or aryl group represented by $R^{32}$ and the aryl group represented by $R^{33}$ can also be substituted with other substituents, for example, an alkyl group, an aryl group, an alkoxy group, an aryloxy group, an amido group, an N-alkylsulfamoyl group, N-alkylcarbamoyl group, an acyloxy group, a carboxy group, a sulfo group, a sulfonamido group, a halogen atom, etc.

The following couplers are illustralive however they are not to be construed as limiting the present invention.

C-1

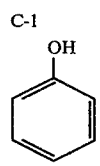

C-2

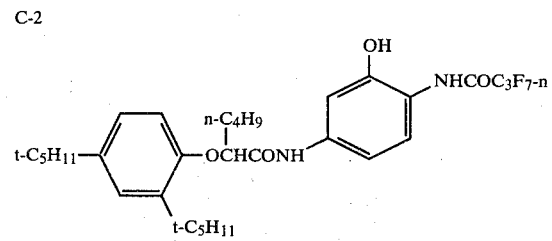

C-3

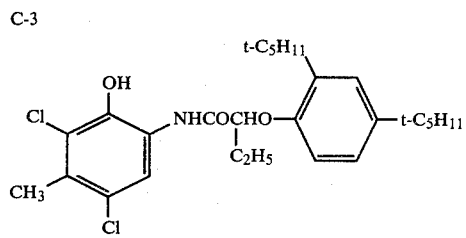

C-4

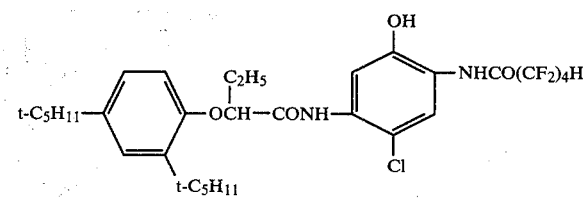

C-5

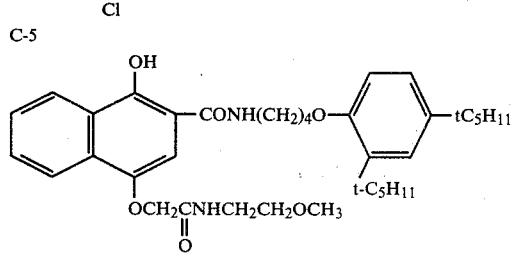

C-6

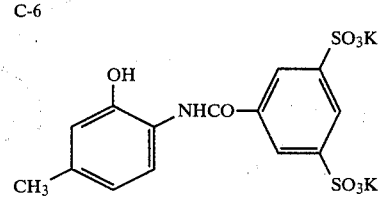

C-7

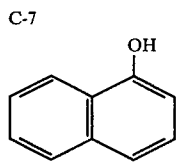

C-8

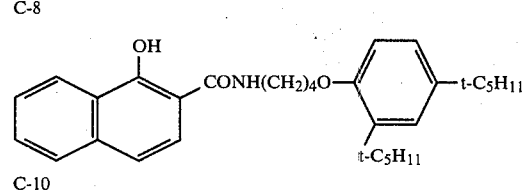

C-9

C-10

C-11
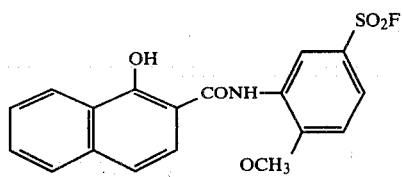
C-12
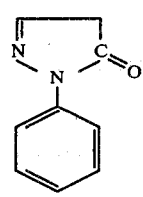
C-13
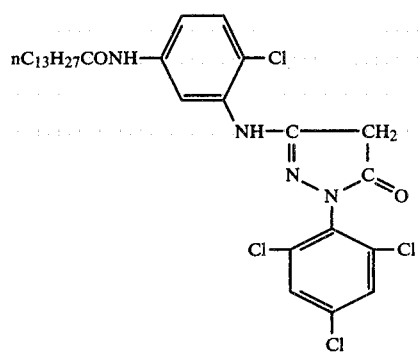
C-14
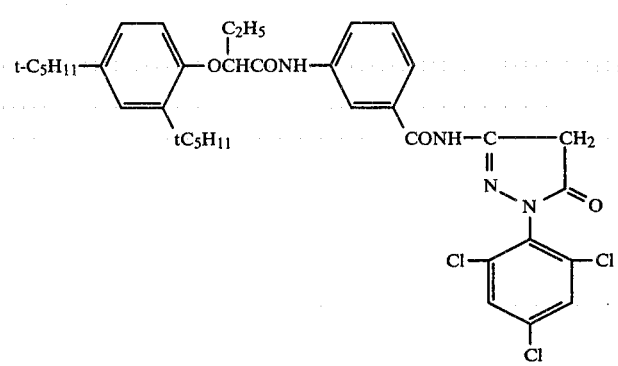
C-15
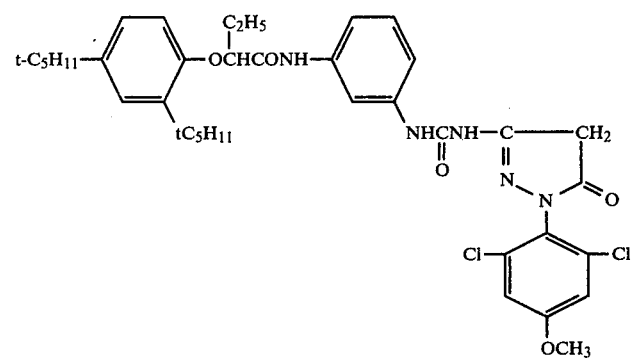
C-16
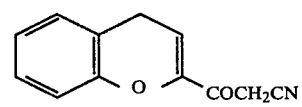
C-17
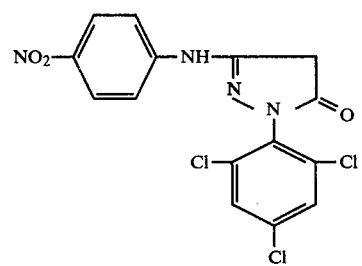
C-18
CN—CH₂—CN

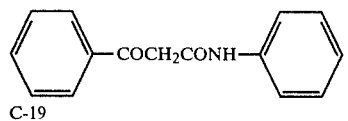
C-19
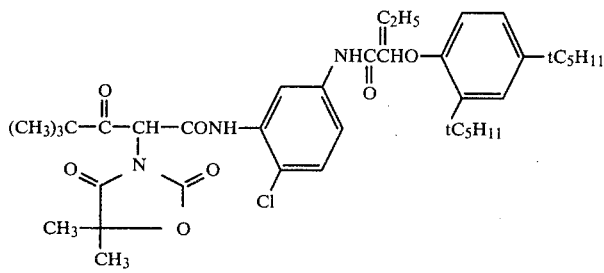
C-20
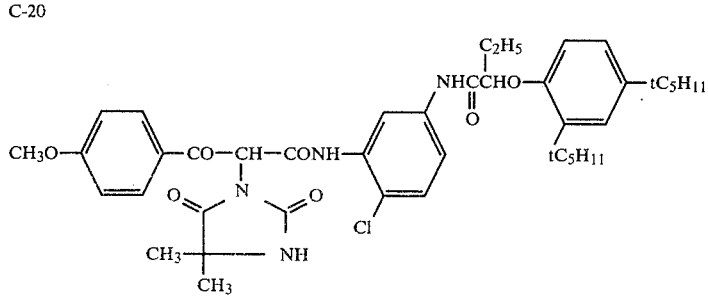
Other dyes to which the present invention is applicable are exemplified by the following compounds.
D-21
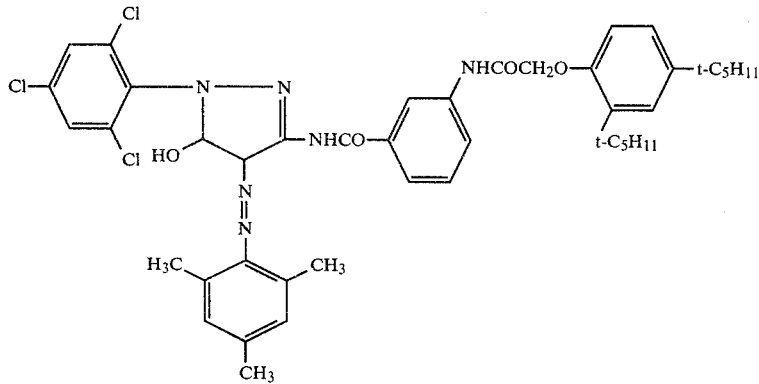
D-22
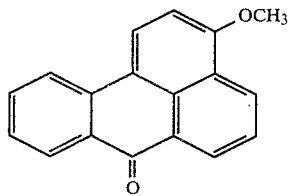
D-23
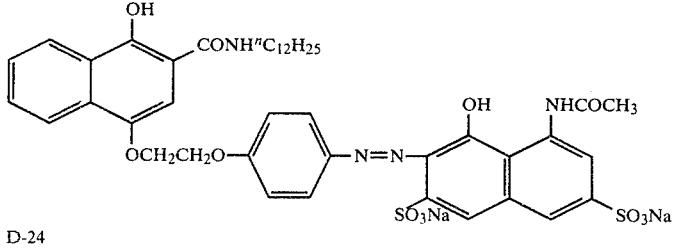
D-24

-continued
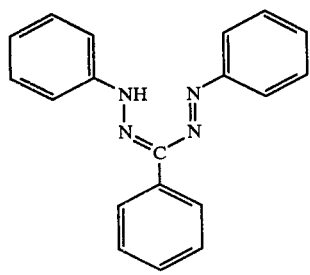
D-25
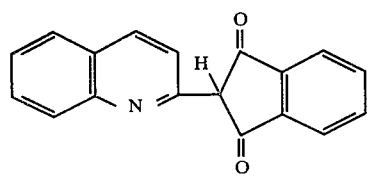
D-26
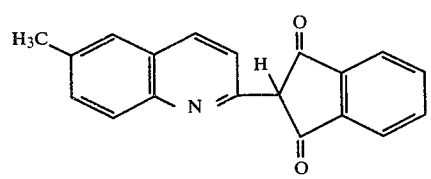
D-27
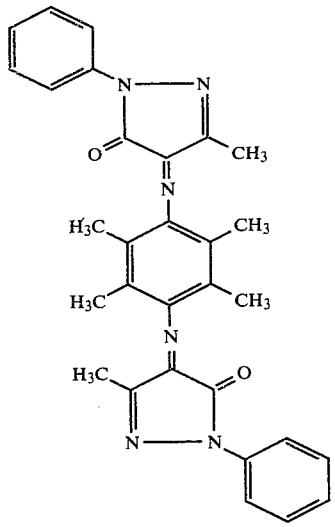
D-28
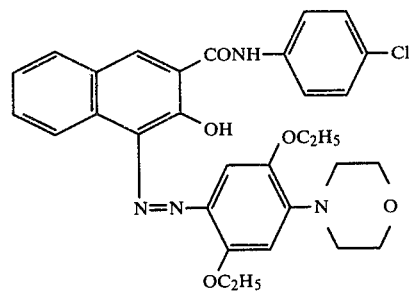
D-29

-continued
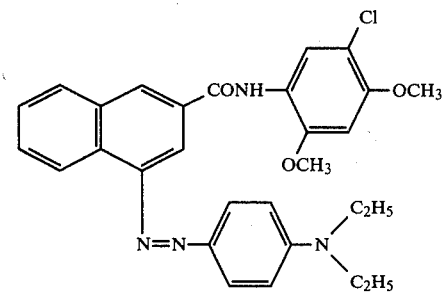
D-30
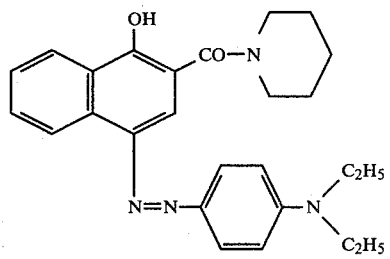
D-31
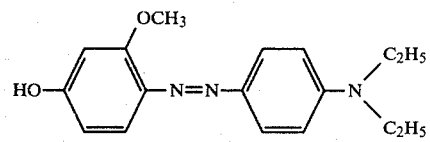
D-32
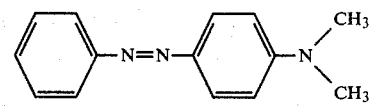
D-33
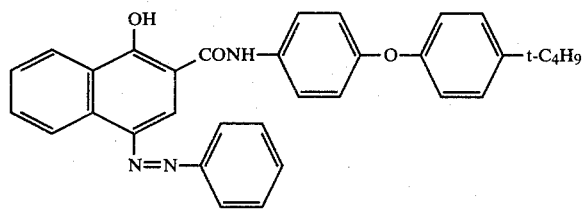
D-34
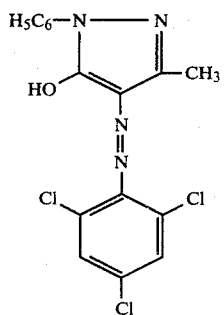
D-35

-continued
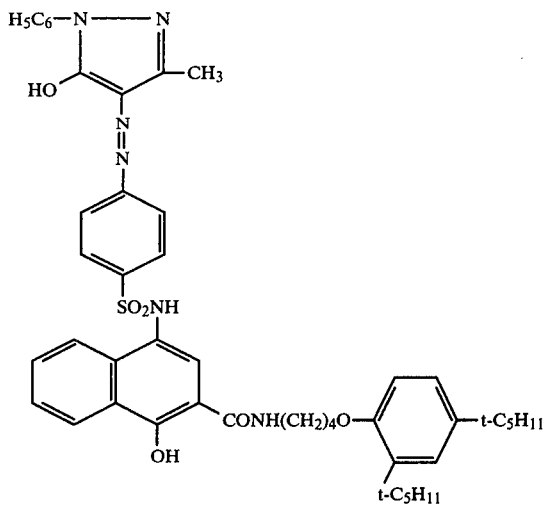
D-36
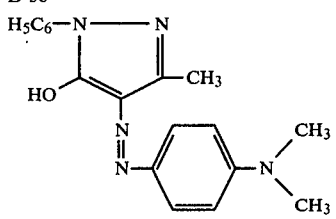
D-37
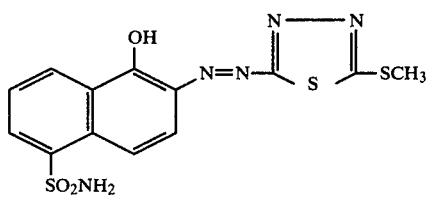
D-38
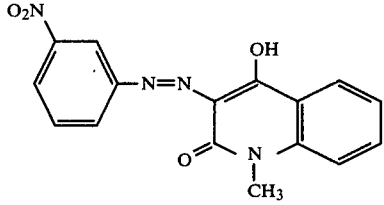
D-39
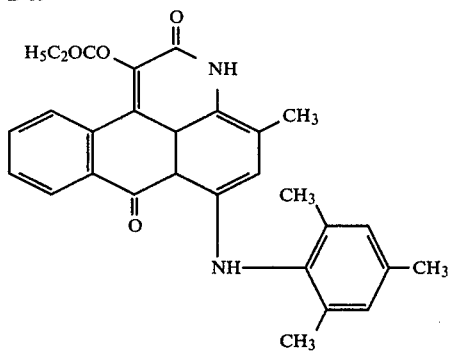
D-40
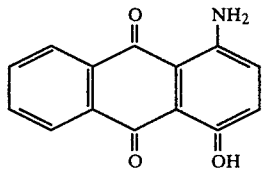

-continued
D-41
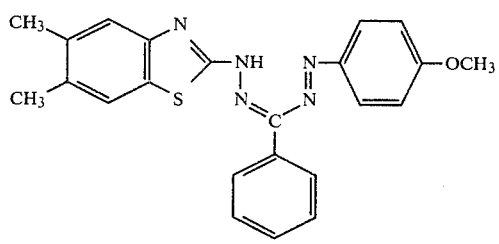
D-42
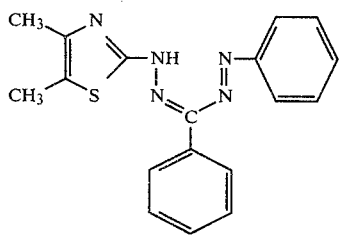
D-43
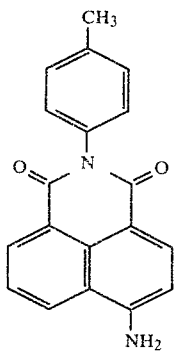
D-44
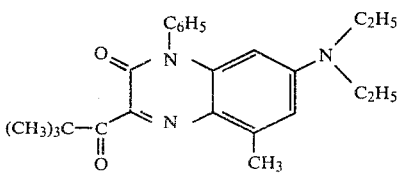
D-45
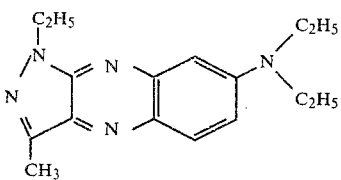
D-46
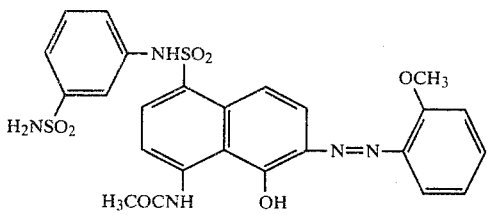
D-47

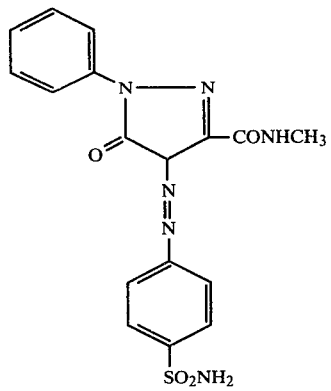
D-48
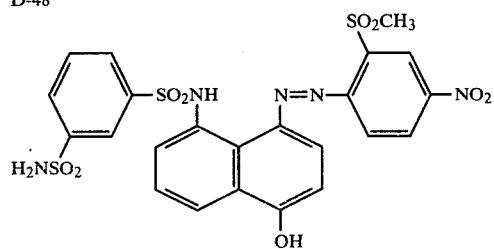
D-49
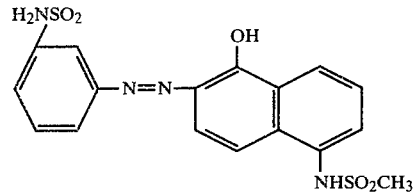
D-50
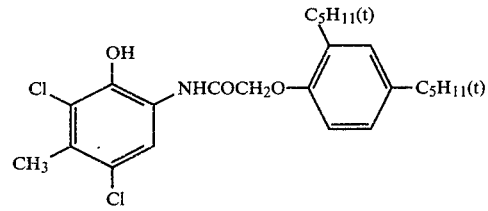
D-51
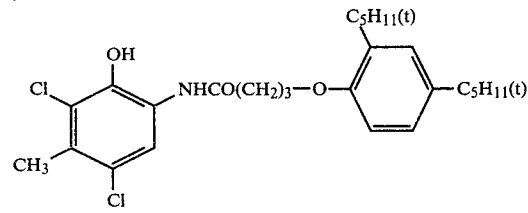
D-52
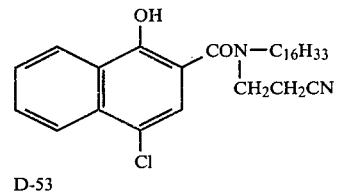
D-53
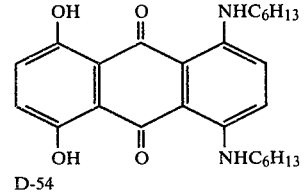
D-54

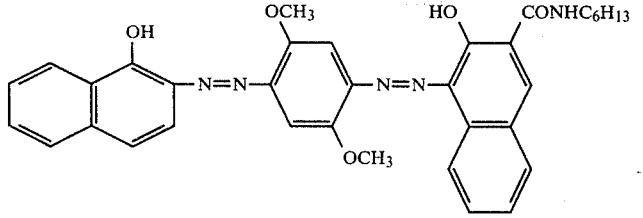
D-55
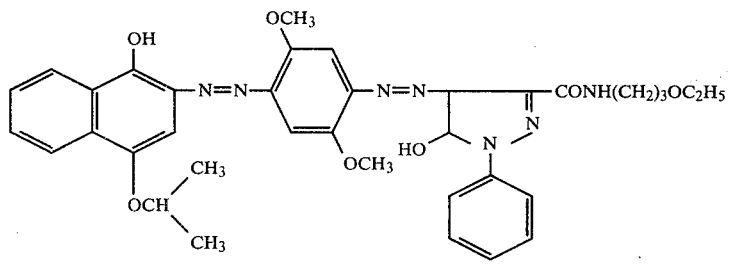
D-56
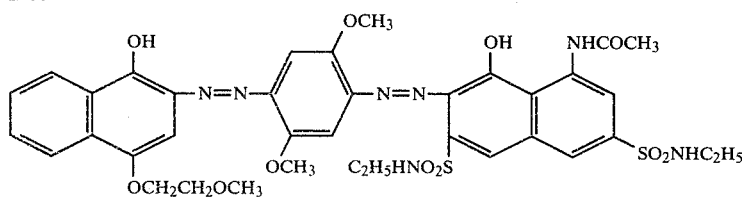
D-57
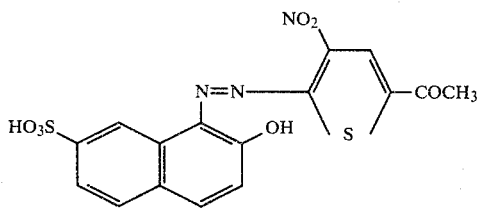
D-58
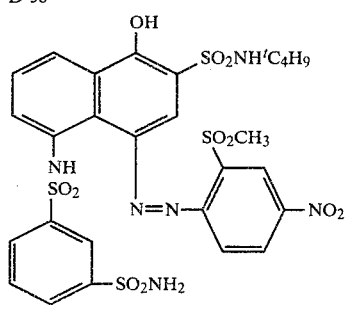
D-59
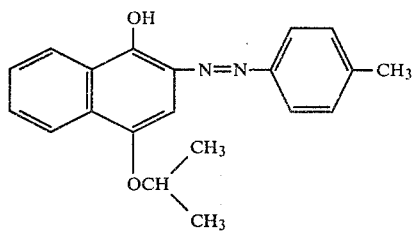
D-60
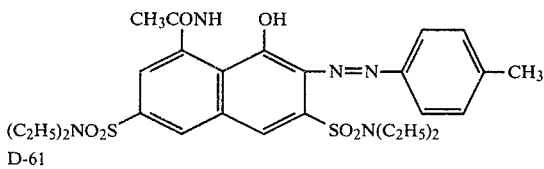
D-61

-continued
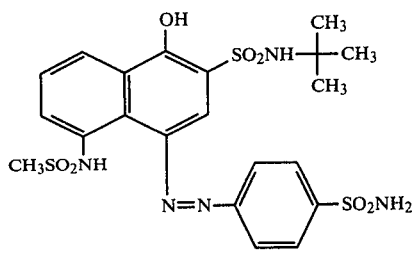
D-62
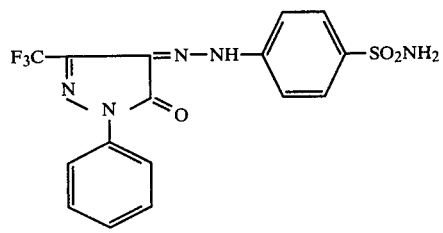
D-63
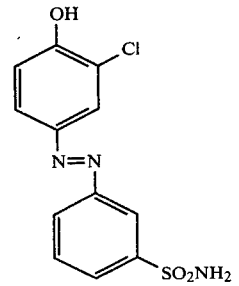
D-64
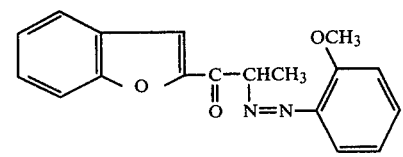
D-65
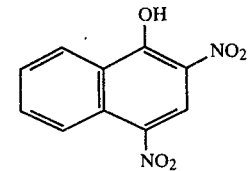
D-66
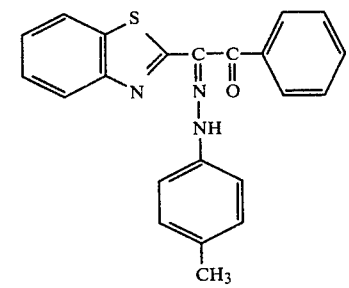
D-67
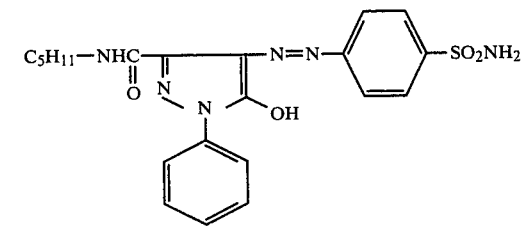

D-68

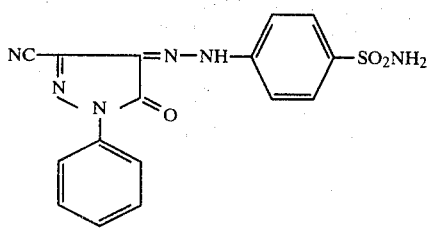

D-69

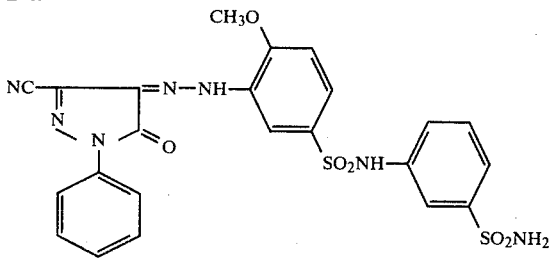

D-70

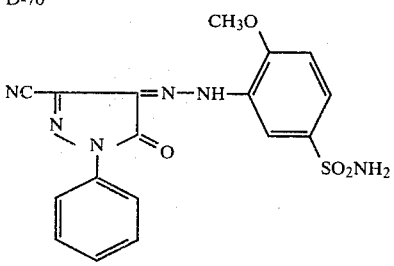

Still other types of dye to which the present invention can be preferably applied include those which are formed by the oxidation of DRR compounds described in the following patents and disclosure; U.S. Pat. Appln. Ser. No. B351,673, U.S. Pat. Nos. 3,932,381, 3,928,312, 3,931,144, 3,954,476, 3,929,760, 3,942,987, 3,932,380, 4,013,635 and 4,013,633, Publd. Japan. Pat. Appln. (OPI) Nos. 113,624/1976, 109,928/1976, 104,343/1976 and 4,819/1977, Japan. Pat. Appln. No. 64,533/1977, corresponding to published Japanese Patent Application (OPI) No. 149328/78, "Research Disclosure" (1976 Nov.) pp 68/74, No. 13024, etc.

Also, the instant invention is applicable to those dyes that are released or formed as a result of reaction between DDR coupler and the oxidation product of a color developing agent; such DDR couplers are disclosed in, for example, Brit. Pat. Nos. 840,731, 904,364, 932,272, 1,014,725, 1,038,331, 1,066,352 and 1,097,064, Publd. Japan. Pat. Appln. (OPI) No. 133,021/1976, (U.S. Defensive Publication), No. T900,029, U.S. Pat. No. 3,227,550, etc.

The present invention is also applicable to dye developers set forth in Publd. Japan. Pat. Applns. (OPI) Nos. 182/1960, 18,332/1960, 32,130/1973, 43,950,1971 and 2,618/1974, etc.

Still other types of dyes to which the instant invention is applicable include those employed in silver dye bleach process; such yellow dyes are exemplified by azo dyes such as Direct Fast Yellow GC (C.I. 29000), Crysophenine (C.I. 24895), etc., benzoquinone dyes such as Indigo Golden Yellow IGK (C.I. 59101), Indigosol Yellow 2GB (C.I. 68420), Mikethrene Yellow GC (C.I. 67300), Indanthrene Yellow 4GK (C.I. 68405), Argosol Yellow GCA-CF (C.I. 67301), Indanthrene Yellow GF (C.I. 68420), etc., anthraquinone dyes, soluble vat dyes with fused ring structures, other types of vat dye, etc. Magenta dyes are exemplified by azo dyes such as Sumilite Supra Rubinol B (C.I. 29225), Benzobrilliant Gelanine B (C.I. 15080), etc., indigoid dyes such as Indigosol Brilliant Pink IR (C.I. 73361), Indigosol Violet 15R (C.I. 59321), Indigosol Red Violet IRRL (C.I. 59316), Indanthrene Red Violet RRK (C.I.67895), Mikethrene Brilliant Violet BBK (C.I. 6335), etc., soluble vat dyes comprising anthraquinone-hetero-polycyclic compounds, and still other types of vat dye. Cyan dyes include azo dyes such as Direct Sky Blue 6B (C.I. 24410), Direct Brilliant Blue 2B (C.I. 22610), Sumilite Supra Blue (C.I. 34200), etc., phthalocyanine dyes such as Sumilite Supra Turkeys Blue G (C.I. 74180), Mikethrene Brilliant Blue 4G (C.I. 74140), etc., Indanthrene Turkeys Blue 5G (C.I. 69845), Indanthrene Blue GCD (C.I. 73066), Indigosol 04G (C.I. 73046), Anthrasol Green IB (C.I. 59826), etc.

The metal chelate complex associated with the instant invention acts to stabilize organic substrate materials to color fading, and can be incorporated in at least one layer making up the emulsion coatings of a color photographic film product.

The substrate material and the complex each can be present in one or more of the hydrophilic colloid layers making up a photographic element. It is preferred that the metal chelate complex and the organic substrate material be present (i.e., coexist) in the same emulsion layer, of course, the effect of the present invention can also be attained when the complex and substrate are present in contiguous layers inasmuch as diffusion is allowed to occur between the layers. Were any (further) undesirable diffusion to occur, conventional mordanting techniques could be applied to the present invention. The substrate and complex can be present in non light-sensitive layers as well, such as the dye image receiving member used in the photographic diffusion transfer film unit. In the case of image transfer units, the metal chelate complex is preferably located in a layer where dye images are finally found, i.e., in an image-receiving layer. Usually, the dye images formed in the image-receiving layer do not diffuse further into any other layer(s) so the complex is generally used in the image-receiving layer. When the substrate material and the complex are contained in a non light-sensitive image recording element, they are preferably mordanted. In such a case, the chelate complex possesses a ligand suitable for holding the complex in the mordanted layer of the image-receiving element so that the complex does not diffuse and leave the vicinity of the dye substrate to be stabilized. However, using the mordanting techniques effectively, the chelate complex can be incorporated in any other layer adjacent the image-receiving layer, as long as diffusion is effected and the chelate complex interacts with the dye images to improve light fastness.

Various types of image transfer film unit can be designated as well suited for the practice of the instant invention. One is imbibition transfer film unit set forth in U.S. Pat. No. 2,882,156. The present invention can further be applied to the color image transfer film unit described in U.S. Pat. Nos. 2,087,817, 3,185,567, 2,983,606, 3,253,915, 3,227,550, 3,227,551, 3,227,552, 3,415,646, 3,594,164 and 3,594,165 and Belg. Pat. Nos. 757,959 and 757,960.

Efficient methods of dispersing these metal chelates include those known and employed for the dispersion of couplers. U.S. Pat. Nos. 2,304,939 and 2,322,027 disclose the use of lowvolatile organic solvents for the dissolution of metal chelates. Other methods applicable to the present purpose include those described in U.S. Pat. Nos. 2,801,170, 2,801,171 and 2,949,360 wherein low-boiling point or water-soluble organic solvents are employed in conjunction with low-volatile solvents.

Low-volatile solvents effectively used for the dispersion of the organic substrate material as well as the metal chelate involved in the instant invention include di-n-butyl phthalate, benzyl phthalate, triphenyl phosphate, tri-o-cresyl phosphate, diphenylmono-p-tert-butylphenyl phosphate, monophenyl-di-p-tertbutylphenyl phosphate, diphenylmono-o-chlorophenyl phosphate, monophenyldi-o-chlorophenyl phosphate, 2,4-di-n-amylphenol, 2,4-di-t-amylphenol, N,N-diethyllaurylamide, trioctyl phosphate, and trihexyl phosphate both of which are set forth in U.S. Pat. No. 3,676,137, etc.

Volatile and/or water-soluble organic solvents which can be used in conjunction with the above-cited low volatile solvents are those described in, for example, U.S. Pat. Nos. 2,801,171, 2,801,170 and 2,949,360, including; (1) Solvents which are substantially imiscible with water such as methyl acetate, ethyl acetate, propyl acetate, butyl acetate, isopropyl acetate, ethyl propionate, sec-butyl alcohol, ethyl formate, butyl formate, nitromethane, carbon tetrachloride, chloroform, etc., and (2) Water-miscible organic solvents such as, for example, methyl isobutyl ketone, β-ethoxyethyl acetate, β-butoxytetrahydrofurfuryl adipate, diethylene glycol monoacetate, methoxytriglycol acetate, acetonylacetone, diacetone alcohol, ethylene glycol, diethylene glycol, dipropylene glycol, acetone, methanol, ethanol, acetonitrile, dimethylformamide, dioxane, etc.

The complex compound and the substrate material embodying the invention can be used together with the materials described in "Product Licensing Index" vol. 92, No. 9232 (1971, Dec.), pp 107-110 according to the methods also described therein. Reference is made to Chapters I, II, III, IV, V, VI, VII, VIII, IX, X, XI, XII, XIII, XIV, XV, XVI, XVII, XVIII and XXII.

In general, the complex of the formula (I) is dissolved or suspended in an appropriate solvent which is chosen, depending upon the physical properties of the complex used, from water, water-miscible and water-immiscible organic and inorganic solvents (the details of which are described in U.S. Pat. No. 3,966,468) and the organic substrate material is dissolved or suspended therein. Alternatively, again depending upon the physical properties of the compounds; solutions and/or dispersions may be prepared separately and subsequently mixed. For example, a fluorescent whitening agent may be dissolved or suspended in an organic or inorganic solvent such as water or dimethylformamide, etc., together with the complex of the present invention or separately; and the mixture may be coated onto or incorporated into a suitable base substance. An adjacent double layer coating is possible and in some cases may be preferred if some diffusion between the contiguous layers occurs and light fastness improvement is effected. Where it is desired to improve the light fastness in a colored polymer for use of agricultural vinyl sheets, the colored polymer and complex of the formula (I) are likewise mixed in the form of a solution, dispersion, etc., followed by extrusion molding, etc., in a conventional manner.

The colored polymer as used herein is a polymer containing a coloring material in a state of molecular dispersion or melt. The polymer is represented by natural resins other than gelatin, e.g., cellulose and derivatives thereof, vinyl resins, polycondensates, silicone resins, alkyd resins, polyamides, paraffin and mineral waxes as described in U.S. Pat. No. 3,966,468.

Turning now to the amount of the complex, any addition of the complex will bring about an improvement in light fastness to some extent, and theoretically there is no upper limit on the amount of the complex which may be added. Preferably, the complex is present in a amount of at least 0.1 mol % based on 1 mol of the organic substrate material, more preferably, in an amount of 0.1 to 1000 mol %, and most preferably, in an amount of 1 to 300 mol %. In the case of a photographic material, the amount is often expressed in a weight unit per square meter of photographic material which can be calculated from the parameters set out above. For convenience, however, in the case of a photographic material, the complex is preferably present in an amount of at least 1.0 micromole per square meter of the photographic product, and more preferably in an amount of from about 10 to $1. \times 10^4$ micromoles per square meter of product.

The concentration of the substrate material corresponds in general to that for the image forming material usually adopted in color photographic technology. As is well known to those skilled in the art, the substrate material is preferably present in the range of from about 10 to $10^4$ micromoles per square meter of the photographic product. A more preferably range is from about 100 to about $3 \times 10^3$ micromoles per square meter of the photographic product.

The substrate material involved in the instant invention usually has the absorption peak at a wavelength shorter than about 800 nm. This peak should preferably be in the range of from about 300 to 800 nm, and more preferably from about 400 to 800 nm.

Any type of support material ordinarily employed in photographic products can be used in the instant invention, including, for example, cellulose nitrate film, cellulose acetate film, cellulose acetate butyrate film, cellulose acetate propionate film, polystyrene film, poly(ethylene terephthalate) film, polycarbonate film, laminated sheet materials comprising the above-mentioned films, paper, etc. Especially suited are baryta coated paper, paper laminated or coated with an α-olefin polymer such as polyethylene, polypropylene and the like comprising $C_2$–$C_{10}$ α-olefins, those plastic films that are disclosed in Publd. Examd. Japan. Pat. Appln. No. 19,068/1972 which are provided with a roughned surface of an improved adhesive property to different polymeric materials, etc.

To prepare a photographic light-sensitive material for the present invention, various hydrophilic colloids are employed. Hydrophilic colloid materials used as the binder for the photographic emulsion coating and/or other additional coatings include, for example, gelatin, colloidal albumin, casein, cellulose derivatives such as carboxymethylcellulose, hydroxyethylcellulose, etc., carbohydrate derivatives such as agar-agar, sodium alginate, starch and its derivatives, etc., synthetic hydrophilic polymers such as poly(vinyl alcohol), poly(N-vinylpyrrolidone), acrylic acid containing copolymers, maleic anhydride copolymers, polyacrylamide, derivatives from these synthetic polymers including partially hydrolized products thereof, etc. If necessary, two or more of these colloidal materials are used in combination provided that they are mutually compatible.

Among these most extensively used is gelatin, which can be replaced totally or partially with synthetic polymeric materials or with so-called gelatin derivatives in a manner well known in the art. Such gelatin derivatives can be prepared by modifying or treating gelatin with reagents which have a functional group capable of reacting with the reactive groups contained in the gelatin molecule such as amino, imino, hydroxy or carboxy group, or by grafting to the gelatin molecular chain to a suitable, synthetic polymer chain.

The photographic emulsion coating or other additional coatings composing the photographic product used for the instant invention can involve synthetic polymer materials such as, for example, a latex of vinyl polymer dispersed in water and those which can improve the dimensional stability of the final product. The photographic product can contain one or more of such polymeric materials, and, in some cases, contain them in conjunction with a hydrophilic, water-permeable colloid.

Silver halide photographic emulsions used in the instant invention are usually prepared by mixing an aqueous solution of a water-soluble silver salt (e.g., silver nitrate) with an aqueous solution of a water-soluble halide salt (e.g., potassium bromide) under the presence of a water-soluble polymeric material such as gelatin. The resulting silver halide includes not only silver chloride and silver bromide, but those containing halogen mixtures such as chlorobromide, iodobromide, chloroiodobromide, etc. Any methods well known in the art can be adopted to prepare grains of such a silver halide, including self-evidently single and double jet methods, control double jet method, etc. One can also blend two or more kinds of silver halide photographic emulsion each of which has been prepared independently.

A number of additives can be incorporated in the photographic emulsion in order to prevent the deterioration of photographic speed or the generation of fog during the manufacturing operations, the storage period and photographic processing. Such additives include various heterocyclic compounds such as 4-hydroxy-6-methyl-1,3,3a,7-tetrazaindene, 3-methylbenzothiazole, 1-phenyl-5-mercaptotetrazole, etc., Hg containing compounds, mercapto compounds, metal salts, etc.

The photographic emulsion used in the present invention can be chemically sensitized according to known methods. Chemical sensitizers include gold compounds such as chloroaurates, gold trichloride, etc., salts of noble metals such as Pt, Pd, Ir, Rd, etc., those sulfur compounds that can react with silver salts to yield silver sulfide (e.g., sodium thiosulfate), and other reducing substances such as stannous salt, amine, etc.

The photographic emulsion used in the present invention can be spectrally sensitized or super-sensitized by the use of cyanine dyes such as cyanine, merocyanine, carbocyanine individually or assortedly among themselves or with styryl type dyes. The selection of dyes depends on the spectral region to be sensitized, the degree of spectral sensitivity, etc., which vary by the expected application of the resulting product.

The hydrophilic colloid contained in the photographic material used in the instant invention can be, if desired, cross-linked with a variety of hardening agents such as, for example, aldehydes, active halogen compounds, vinylsulfones, carbodiimides, N-methylol compounds, epoxy compounds, etc.

According to one embodiment of the instant invention where the method of the invention is applied to a color photographic product, the color photographic material is, after imagewise exposure, processed in the ordinary manner to provide color images. Such processing comprises color development, bleaching and fixing, to which other steps such as rinsing with water or stabilization may be introduced if necessary. Some of these processing operations can be combined into a mono-bath step; a typical example is the so-called "blix" comprised of bleaching and fixing agents. The color development is carried out in an alkaline solution containing an aromatic primary amine developing agent. Preferable compounds as the developing agent include Compound (A) to (L) illustrated above.

As another embodiment, the method of the instant invention is applied to a color photographic product of diffusion transfer type. In this case the processing is effected within the photographic material automatically. Suitable developing agents which are contained in a rupturable container include, in addition to Compounds (A) and (L), N-methylaminophenol, 1-phenyl-3-pyrazolidone, 1-phenyl-4,4-dimethyl-3-pyrazolidone, 1-phenyl-4-methyl-hydroxymethyl-3-pyrazolidone, 3-methoxy-N,N-diethyl-p-phenylenediamine, etc.

For the formation of color images in the photographic products used in the instant invention, various methods can be employed which are based on the following principles: (i) the coupling reaction between a dye-forming color coupler and the oxidation product from a p-phenylenediamine type chromogenic developing agent, (ii) processing using a dye developer, (iii) an oxidative cleavage reaction of a DRR compound, (iv) the dye-releasing reaction caused by the coupling of a DDR coupler, (v) a dye-forming reaction caused by the coupling of a DDR coupler, (vi) silver dye bleach process and other conventionally known processes.

As is evident from the description heretofore, the method of the instant invention can be applied to a wide variety of color photographic materials such as color positive film, color printing paper, color negative film, color reversal film, film units for color diffusion transfer, silver dye bleach photographic material, etc.

EXAMPLE 1

Into a mixture comprising 3 ml trioctyl phosphate and 5 ml ethyl acetate was dissolved 0.1 g of a dye having the following structure.

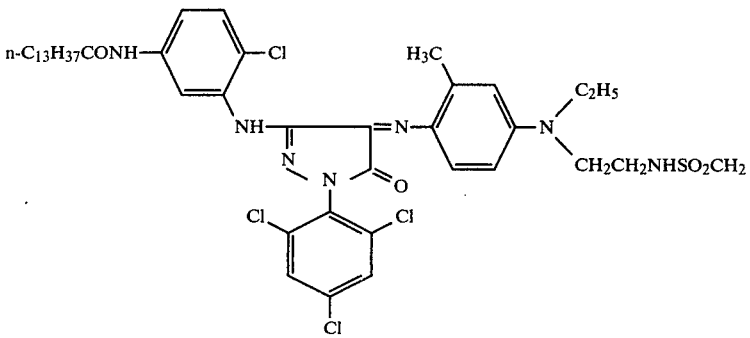

The resulting solution was emulsified into 10 g of a 10% aqueous gelatin solution containing 1 ml of a 1% sodium dodecylbenzenesulfonate aqueous solution.

This emulsified dispersion was mixed with 10 g of a 10% gelatin solution and then spread onto a substrate comprising a paper support laminated with polyethylene films on both surfaces and dried to give Sample A.

Another sample (Sample B) was prepared in a similar manner except that 50 mg of Compound I-2 characteristic of the present invention was to the emulsified dispersion. Further, Samples C and D were prepared similarly but with the addition of 2,5-ditert-octylhydroquinone, a conventional fade preventing agents, in an amount of 0.02 for C and 0.2 for D, respectively. The coating rate of the dye was 60 mg/m$^2$ and of Compound I-2 was 30 mg/m$^2$.

In a Xenon Tester (Light Intensity; 200,000 luxes), a 48 hour fading test was performed on pieces of these samples superimposed with a UV cut filter C-40, a product of Fuji Photo Film Co.

The results of the test are shown in Table 1 by the density values obtained by the measurement with Macbeth Densitometer RD 514 loaded with a green filter of status AA grade.

Table 1

| Sample | Initial density | Density after 48 hour fading test |
|---|---|---|
| A | 0.85 | 0.05 |
| B | 0.83 | 0.70 |
| C | 0.83 | 0.05 |
| D | 0.86 | 0.50 |

The table reveals the superior effect of the complex of the instant invention for fade prevention in comparison with the conventionally known fade preventing agents used in Samples C and D. It should be noted that in Samples B and C equivalent moles of the fade preventing agents are present. Comparison of B with D shows that even ten times amount of the conventional fade preventing agent is less effective than the complex composing the present invention.

EXAMPLE 2

0.1 g of Compound C-23 was mixed with 0.2 ml of 1 N NaOH and then added to 2 ml methanol. The solution obtained was poured into 10 g of a 10% gelatin solution. The resulting mixture was coated on a support comprising a paper base laminated on both sides with polyethylene film so as to give a coating rate of 80 mg/m$^2$ for Compound C-23. This photographic paper was designated Sample E.

Similar operations were repeated to provide Sample F with a further addition of 50 mg, Compound I-22 characterizing the instant invention. For the purpose of comparison Sample G was prepared by the adding of 100 mg of the following compound instead of Compound I-22.

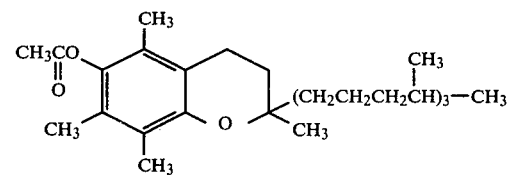

A 15 hour fading test was carried out taking care to cutout UV light as in Example 1. The results are shown in Table 2. The Macbeth Densitometer was again used for density measurement.

Table 2

| Sample | Initial Density | Density after 15 hour fading test |
|---|---|---|
| E | 0.90 | 0.03 |
| F | 0.88 | 0.50 |
| G | 0.90 | 0.10 |

Table 2 clearly shows the excellent effect of the compound characterizing the present invention for fade retardation.

EXAMPLE 3

10 g of a magenta coupler, 1-(2,4,6-trichlorophenyl)-3-[2-chloro-5-tetradecaneamide]anilino-2-pyrazolino-5-one was dissolved in a mixture consisting of 20 ml tricresyl phosphate, 5 ml dimethylformamide and 15 ml ethyl acetate, and the resulting solution was emulsified in 80 g of a 10% gelatin solution containing 8 ml of a 1% aqueous sodium dodecylbenzenesulfonate solution. Then the dispersion was mixed into 145 g of a green sensitive silver chlorobromide emulsion which contained 7 g of silver (the bromide content in the silver halide was 70 mole %). After the addition of a hardening agent and a coating aid, the mixture was spread over a support comprising a paper base laminated on both sides with polyethylene film to give Sample H. The coating rate of the coupler was 400 mg/m².

By repeating similar procedures, Samples I and J were prepared wherein Compound I-11 of the instant invention was added for Sample I in an amount of 0.5 g to provide a coating amount of 20 mg/m² and 0.5 g of the following compound was used for Sample J in a coating amount of 20 mg/m².

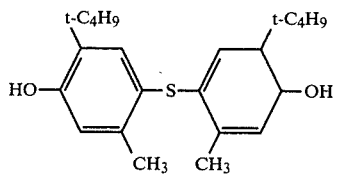

After exposure, each of these samples was processed with the following processing solutions.

| Developer | |
|---|---|
| benzyl alcohol | 15 ml |
| diethylenetriamine penta-acetate | 5 g |
| KBr | 0.4 g |
| Na₂SO₃ | 5 g |
| Na₂CO₃ | 30 g |
| hydroxylamine hydrosulfate | 2 g |
| 4-amino-3-methyl-N-ethyl-N-β-(methanesulfonamide)ethyl-aniline . 3/2H₂SO₄—H₂O | 5 g |
| water to make | 1000 ml |
| pH | 10.1 |
| Blix solution | |
| ammonium thiosulfate (70 wt.%) | 150 ml |
| Na₂SO₃ | 5 g |
| Na[Fe(EDTA)] | 40 g |
| EDTA | 4 g |
| water to make | 1000 ml |
| pH | 6.8 |
| Processing conditions | |
| development | 33° C., 3 min. 30 sec. |
| blix | 33° C., 1 min. 30 sec. |
| rinse with water | 28°-35° C., 3 min. |

Each sample provided with a dye image was exposed to sunlight through a UV cut filter C40 (a product of Fuji Photo Film Co. which eliminated light with wavelength shorter than 400 nm) for 2 weeks.

The results are summarized in Table 3. The degree of fading was expressed by the density drop at the area with the initial density of 2.0. The density was measured with a Macbeth Reflective Densitometer RD 514 (with a Status AA filter).

Table 3

| Sample | Density drop by fading test | |
|---|---|---|
| H | 1.20 | comparison (blank) |
| I | 0.20 | invention |
| J | 0.70 | comparison |

The table demonstrates the superior fade retarding effect of the complex compound of the instant invention.

EXAMPLE 4

10 g of a magneta coupler, 1-(2,4,6-trichlorophenyl)-3-]2-chloro-5-tetradecanamide]anilino-2-pyrazolino-5-one was dissolved in a mixture of 30 ml trioctyl phosphate, 5 ml dimethyl-formamide and 15 ml ethyl acetate. The resulting solution was dispersed in 80 g of a 10% aqueous gelatin solution containing sodium dodecylbenzenesulfonate.

Then the dispersion was poured into 145 g of a green sensitive silver chlorobromide emulsion which contained 7 g of silver (the bromide content in the silver halide was 70 mole %). After the addition of a hardening agent and a coating aid, the mixture was spread over a support comprising a paper base laminated on both sides with polyethylene film to give Sample K. The coating rate of the coupler was 400 mg/m². By repeating similar procedures, Samples L and M were prepared wherein Compound I-17 of the instant invention was added to the emulsion for L in an amount of 0.5 g to provide a coating amount of 20 mg/m² and 2.0 g of the following compound for M in a coating amount of 80 mg/m².

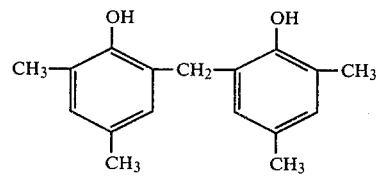

These examples were exposed and processed in the same manner as in Example 3. The fading test was also carried out according to the method described in Example 3. The results are shown in Table 4.

Table 4

| Sample | Density drop by fading test | |
|---|---|---|
| K | 0.80 | comparative sample |
| L | 0.15 | instant invention |
| M | 0.50 | comparative sample |

The table demonstrates the superior fade retarding effect of the compound of the instant invention.

EXAMPLE 5

A solution of 50 mg of a dye having the following structure:

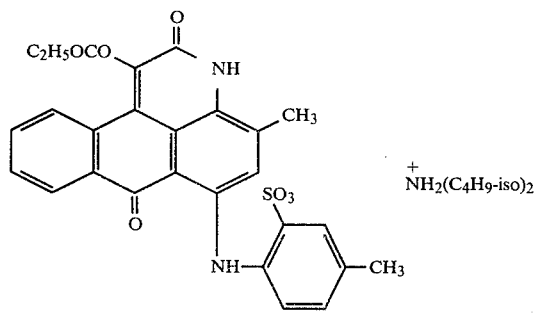

and 500 mg of polycarbonate Lexan 145 (tradename, manufactured by General Electric Co.) in 100 ml of dichloromethane was coated onto a glass plate using a spinner. A film having a thickness of 5.5 μm. which was magenta-colored was thus provided on the glass plate (Sample A).

In a similar manner, a colored film was prepared except that Compound I-2 of the instant invention was further incorporated into the solution (Sample B).

The coating rates were as follows.

Dye: 500 mg/m²
Compound I-2: 50 mg/m²

To test for color facing the thus obtained films were exposed to sunlight for one month. The results obtained are shown in Table 5, in which the density was measured at 550 nm.

Table 5

| Sample | Initial density | Density after fading test |
|---|---|---|
| A | 1.0 | 0.50 |
| B | 1.0 | 0.90 |

It can be clearly seen from the results shown in the table that the system of the instant invention showed only a 10% reduction in density even after one month of sunlight exposure, whereas the density of the system for comparison where no chelate complex was present was seriously reduced to 50% of the original density. That is, the system of the instant invention exhibits far superior light fastness to the comparison sample. This test shows that a colored film treated in accordance with the instant invention is suitable for use as an agricultural cover sheets, etc.

EXAMPLE 6

In 20 ml of trioctyl phosphate were dissolved 100 mg of the dye employed in EXAMPLE 1 and 5 mg of Compound I-11 of the instant invention to prepare a solution (Sample A).

For comparison, a solution was prepared in a similar manner except that 5 of Compound IV described in U.S. Patent 4,050,938 and having the following structure:

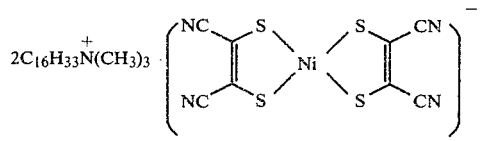

was used instead of Compound I-11 (Sample B).

The thus prepared sample solutions were changed to a glass-made test vessel (diameter, 1 cm), respectively. A color fading test was carried out by exposing the solutions to a Xenon tester (light intensity: 200,000 luxes) for 100 hours and 250 hours. The results are shown in Table 6.

Table 6

| Sample | Dye Remaining (%)* | |
|---|---|---|
| | 100 hrs. | 250 hrs. |
| A | 98 | 95 |
| B | 95 | 10 |

*Dye remaining (%) = $\frac{\text{Density measured at 550 nm after fading test}}{\text{Density measured at 550 nm before fading test}} \times 100$ As can be clearly seen from the results shown in Table 6, the dye remaining is markedly high in the system of the instant invention; whereas, in the prior art system, the dye remaining rate after fading test for 250 hours is seriously reduced.

Briefly summarizing the effects achieved by the metal chelate complex employed in the present invention;
(1) The metal chelate complex is readily soluble in organic solvents.
(2) In addition, the structure of the chelate complex can easily be modified so that it permits a large latitude for obtaining desired solubility.
(3) As a result of the latitude of its solubility, the complex is readily enveloped in oil droplets and as a result, photographically undesired interaction with silver halide (e.g., desensitization) is avoidable.
(4) Due to its extremely light solubility, a small amount of the complex is sufficient to effect light fastness; conversely, a large amount can also be employed as in the case of umbrellas, agricultural vinyl cover sheets, etc.
(5) Where the chelate is used in a photographic element, no adverse effect on photographic properties is encountered.
(6) The complex is the first fading prevention agent suitable for improving the light fastness of cyan dye images.

For the reasons above, the metal chelate complex used in the instant invention provides excellent light fastness.

What we claim is:

1. A method of stabilizing a photographically useful organic substrate material selected from the group consisting of anthraquinone dyes, quinone-imine dyes, azo dyes, azomethine dyes, methine or polymethine dyes, indo-amine dyes, indophenol dyes, indigoid dyes, carbonium dyes, formazane dyes and fluorescent whitening agents having an absorption peak between about 300 nm and about 800 nm to light which comprises making co-exist with said substrate material in an amount sufficient to stabilize said photographically useful organic substrate material against the action of light at least one compound represented by the following general formula (I).

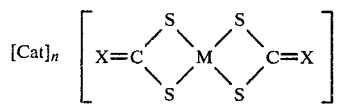

where M represents a metal atom selected from the group consisting of Cu, Co, Ni, Pd and Pt atoms, Cat represents a divalent organic or inorganic cation, or two monovalent organic or inorganic cations, X represents a

group or a sulfur atom, $R^1$ and $R^2$ represent CN, $COR^3$, $COOR^4$, $CONR^5R^6$ or $SO_2R^7$; or $R^1$ and $R^2$ combine to form a non-metallic 5- or 6-membered ring, wherein $R^3$, $R^4$ and $R^7$ represent a substituted or unsubstituted alkyl group having from 1 to 20 carbon atoms, or a substituted or unsubstituted aryl group having from 6 to 10 carbon atoms, $R^5$ and $R^6$ represents a hydrogen atom, a substituted or unsubstituted alkyl group having from 1 to 20 carbon atoms, or a substituted or unsubstituted aryl group having from 6 to 10 carbon atoms and
n is 1 when Cat is a divalent cation and 2 when Cat is a monovalent cation.

2. The method of claim 1, wherein said organic substrate material is a color photographic dye image.

3. The method of claim 1 wherein said chelate compound represented by general formula (I) in incorporated into a medium containing a dye having an absorption peak between about 300 and 800 nm.

4. The method of claim 2, wherein said color photographic dye image is formed from a dye forming color coupler, a DDR coupler, a DRR compound or a dye developer.

5. The method of claims 1 or 2, wherein the compound represented by general formula (I) has a structure represented by the following formulae (IF), (Ig), (Ih) or (Ii).

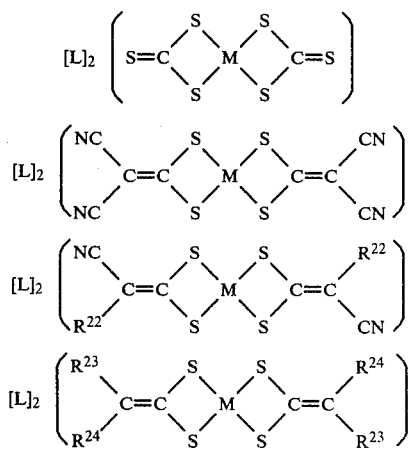

where M represents a metal atom selected from the group consisting of Cu, Co, Ni, Pd and Pt, L represents a cation selected from the group consisting of Li, Na, K, tetraalkylammonium, the alkyl group of which contains from 1 to 18 carbon atoms, and tetraalkylphosphonium the alkyl groups of which contains from 1 to 18 carbon atoms cations, $R^{22}$, $R^{23}$ and $R^{24}$ represent an acyl group, an alkoxycarbonyl group, an alkylsulfonyl group or a carbamoyl group or $R^{23}$ and $R^{24}$ may combine to form a 5- or 6-membered ring.

6. The method of claim 4 wherein said color coupler is a yellow, magenta or cyan dye forming coupler.

7. The method of claim 4 wherein said color photographic dye image is formed upon the reaction of the oxidation product of a primary aromatic amine color developing agent and a coupler selected from the group consisting of benzoylacetanilide and α-pivalylacetanilide yellow dye forming couplers, 5-pyrazolone, indazolone, pyrazolinobenzimidazole, pyrazolo-s-triazole and cyanoacetylcoumarone magenta dye forming couplers, and phenol and naphthol cyan dye forming couplers.

8. A color photographic material comprising at least one layer containing a photographic dye image wherein said layer or an adjacent layer contains a compound of the formula (I) in an amount sufficient to stabilize said photographic material against the action of light

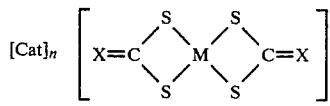

where M represents a metal atom selected from the group consisting of Cu, Co, Ni, Pd and Pt atoms, Cat represents a divalent organic or inorganic cation, or two monovalent organic or inorganic cations, X represents a

group or a sulfur atom, $R^1$ and $R^2$ represent CN, $COR^3$, $COOR^4$, $CONR^5R^6$ or $SO_2R^7$; or $R^1$ and $R^2$ combine to form a non-metallic 5- or 6-membered ring, wherein $R^3$, $R^4$ and $R^7$ represent a substituted or unsubstituted alkyl group having from 1 to 20 carbon atoms, or a substituted or unsubstituted aryl group having from 6 to 10 carbon atoms, $R^5$ and $R^6$ represents a hydrogen atom, a substituted or unsubstituted alkyl group having from 1 to 20 carbon atoms, or a substituted or unsubstituted aryl group having from 6 to 10 carbon atoms and n is 1 when Cat is a divalent cation and 2 when Cat is a monovalent cation.

9. The color photographic material of claim 8, wherein said photographic dye image is formed from a color coupler, a DDR coupler, a DRR compound, or a dye developer.

10. The photographic element of claim 8, wherein said dye is formed by the reaction of a primary aromatic amine color developing agent and a cyan, magenta, or yellow dye image forming coupler.

11. The photographic material of claim 8 wherein said compound is represented by the general formulae

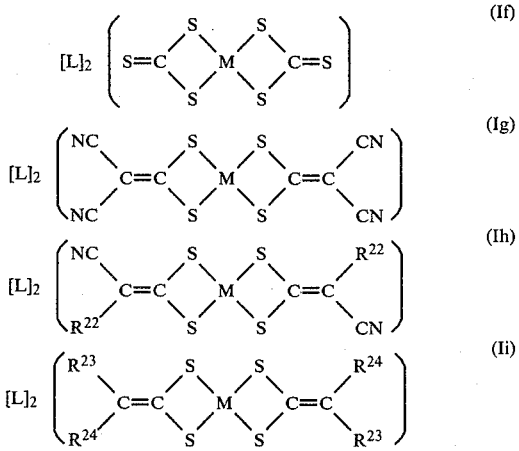

where M represents a metal atom selected from the group consisting of Cu, Co, Ni, Pd and Pt, L represents a cation selected from the group consisting of Li, Na, K, tetraalkylammonium, the alkyl group of which contains from 1 to 18 carbon atoms, and tetraalkylphosphonium the alkyl group of which contains from 1 to 18 carbon atoms cations, $R^{22}$, $R^{23}$ and $R^{24}$ represent an acyl group, an alkoxycarbonyl group, an alkylsulfonyl group or a carbamoyl group or $R^{23}$ and $R^{24}$ may combine to form a 5- or 6-membered ring.

12. The photographic material of claim 8 wherein said color photographic dye image is formed upon the reaction of the oxidation product of a primary aromatic amine color developing agent and a coupler selected from the group consisting of benzolyacetanilide and α-pivalylacetanilide yellow dye forming couplers, 5-pyrazolone, indazolone, pyrazolinobenzimidazole, pyrazolo-s-triazole and cyanoacetylcoumarone magenta dye forming couplers, and phenol and naphthol cyan dye forming couplers.

* * * * *